US008512694B2

(12) United States Patent
Stanford et al.

(10) Patent No.: US 8,512,694 B2
(45) Date of Patent: Aug. 20, 2013

(54) METHOD OF PRODUCING ROUGH STRAINS OF BACTERIA AND USES THEREOF

(75) Inventors: John Lawson Stanford, Tonbridge (GB); Cynthia Ann Stanford, Tonbridge (GB); Graham McIntyre, West Wickham (GB); Oscar Adelmo Bottasso, Coronel Bogado (AR)

(73) Assignee: Bioeos Limited, Surrey (GB)

( * ) Notice: Subject to any disclaimer, the term of this patent is extended or adjusted under 35 U.S.C. 154(b) by 1 day.

(21) Appl. No.: 13/311,208

(22) Filed: Dec. 5, 2011

(65) Prior Publication Data

US 2012/0082699 A1    Apr. 5, 2012

Related U.S. Application Data

(63) Continuation of application No. 12/086,421, filed as application No. PCT/GB2006/004780 on Dec. 19, 2006, now Pat. No. 8,071,354.

(30) Foreign Application Priority Data

Dec. 21, 2005   (GB) .................................. 0526033.6

(51) Int. Cl.
*A01N 63/00*  (2006.01)

(52) U.S. Cl.
USPC ........................................ 424/93.1; 424/93.4

(58) Field of Classification Search
None
See application file for complete search history.

(56) References Cited

U.S. PATENT DOCUMENTS

| | | | |
|---|---|---|---|
| 5,521,300 A | 5/1996 | Shah et al. | |
| 5,525,463 A | 6/1996 | Zolg | |
| 5,599,545 A | 2/1997 | Stanford et al. | |
| 5,721,209 A | 2/1998 | Horwitz et al. | |
| 5,786,326 A | 7/1998 | Horwitz | |
| 5,994,346 A | 11/1999 | Horwitz et al. | |
| 6,136,529 A | 10/2000 | Hammond | |
| 6,218,107 B1 | 4/2001 | Brentano et al. | |
| 6,408,880 B1 | 6/2002 | Kaul | |
| 6,627,203 B1 | 9/2003 | Griffiths et al. | |
| 6,900,204 B2 | 5/2005 | Michaelis et al. | |
| 7,067,500 B2 | 6/2006 | Thornton | |
| 7,078,399 B2 | 7/2006 | Michaelis et al. | |
| 7,122,525 B2 | 10/2006 | Michaelis et al. | |
| 7,252,937 B2 | 8/2007 | Kaltenboeck | |
| 7,662,386 B2 * | 2/2010 | Gaiger et al. | 424/177.1 |
| 2003/0104513 A1 | 6/2003 | Thornton | |
| 2003/0105086 A1 | 6/2003 | Michaelis et al. | |
| 2003/0219788 A1 | 11/2003 | Kaltenboeck | |
| 2004/0014749 A1 | 1/2004 | Michaelis et al. | |
| 2004/0014750 A1 | 1/2004 | Michaelis et al. | |
| 2004/0034021 A1 | 2/2004 | Michaelis et al. | |
| 2004/0037844 A1 | 2/2004 | Rook et al. | |
| 2004/0063718 A1 | 4/2004 | Michaelis et al. | |
| 2006/0013830 A1 | 1/2006 | Bottasso et al. | |

FOREIGN PATENT DOCUMENTS

| | | |
|---|---|---|
| CA | 1 054 055 | 5/1979 |
| EP | 0 556 284 B1 | 6/1997 |
| WO | WO 91/02542 | 3/1991 |
| WO | WO 98/09985 | 3/1998 |
| WO | WO 02/32455 A2 | 4/2002 |
| WO | WO 2004022093 | 3/2004 |
| WO | WO 2005/049056 A2 | 6/2005 |

OTHER PUBLICATIONS

Abbot N. C., et al., "Immunotherapy with *Mycobacterium vaccae* and peripheral blood flow in long-treated leprosy patients, a randomised, placebo-controlled trial," *European Journal of Vascular and Endovascular Surgery* (2002) vol. 24 pp. 202-208.

Barrow, W., et al., "Isolation in high frequency of rough variants of mycobacterium intracellulare lacking c-mycoside glycopeptideollpid antigens," *Journal of Bacteriology* (1982) vol. 150;1, pp. 84-92.

Bauer, M.E., et al., "Chronmic stress in caregivers of dementia patients is associated with reduced lymphocyte sensitivity to glucocrorticoids," *Journal of Neuroimmunology* (2000) vol. 103, pp. 84-92.

Belisle, J., et al., "Chemical basis of rough and smooth variation of mycobacteria," *Journal of Bacteriology* (1989) vol. 171:6, pp. 3465-3470.

Chambers, et al., "Association of bovine papillomavirus with the equine sarcoid," *Journal of General Virology* (2003) vol. 84, pp. 1055-1062.

Choi, Inseon S., et al., "Therapeutic effects of BCG vaccination in adult asthmatic patients: a randomized, controlled trial," *Annals of Allergy, Asthma, and Immunology* (2002) vol. 88 pp. 584-591.

Clerici, M., et al., "$AT_H1 \rightarrow T_H2$ switch is critical step in the etiology of HIV infection," *Immunology Today* (1993) vol. 14:3, pp. 107-111.

Clerici, M., et al., Correlates of protection in HIV infection and the progression of HIV infection to AIDS, *Immunology Letters* (1996) vol. 51 pp. 69-73.

Crisp, Samantha, et al., "Antiendonthelial antibodies after heart transplantation: the accelerating factor in transplant-associated coronary artery disease?" *The Journal of Heart and Lung Transplant* (1994) p. 81-91.

de Roos, N. M., et al., "Effects of probiotic bacteria on diarrhoea, lipid metabolism, and carcinogenesis; a review of papers published between 1988 and 1998," *Am. J. Clinc. Nutr* (2000) vol. 71, pp. 405-411.

(Continued)

*Primary Examiner* — Albert Navarro
(74) *Attorney, Agent, or Firm* — Steptoe & Johnson LLP

(57) ABSTRACT

The present invention relates to a method of producing rough strains of a bacterium, such as *Mycobacterium obuense*, said method comprising exposing said bacterium to a sulfone and/or sulfonamide (such as 4,4'-Diaminodiphenyl sulfone or an analogue thereof). A rough strain of *Mycobacterium obuense* producible by said method and uses thereof. In particular, uses of a rough strain of *Mycobacterium obuense* deposited under the Budapest Treaty at the NCTC with the accession number NCTC 13365.

8 Claims, No Drawings

(56) References Cited

OTHER PUBLICATIONS

Elenkov I. J., et al., "Stress hormones, Th1/Th2 patterns, pro/anti-inlammatory cytokines and susceptibility to disease," *Trends Endocrininol Metab* (1999) vol. 10:9 pp. 359-368.

Elenkov, I.J., et al. "Stress, cytokine patterns and susceptibility to disease," *Bailliere's Clinical Endocrinology Metabolism* (1999) vol. 13:4, pp. 583-595.

Faist, E., et al., "Update on the mechanisms of immune suppression of injury and immune modulation," *World Journal of Surgery* (1996) vol. 20:3, pp. 454-459.

George, Jacob, et al., "Requisite role for interleukin-4 in the acceleration of fatty streaks induced by heat shock protein 65 or *Mycobacterium tuberculosis,*" *American Heart Association* (2000) pp. 1203-1210.

Gill, H.S., et al. "Enhancement of immunity in the elderly by dietary supplementation with the probiotic *Bifidobacterium lactic HN019*[1-3]," *Am. J. Clin. Nutr.* (2001) vol. 74:6 pp. 833-839.

Gill, H.S., et al., "Dietary probiotic supplementation enhances natural killer cells activity in the elderly: an investigation of age-related immunological changes," *Journal of Clinical Immunology* (2001) vol. 21:4, pp. 264-271.

Ginaldi L., et al., "The immune system in the elderly: innate immunity," *Immunologic Research* (1999) vol. 20:2 pp. 117-126.

Goronzy, J. J., et al., "Value of Immunological markers in prdicting responsiveness to Influenza vaccination in elderly individuals," *Journal of Virology* (2001) vol. 75:24 pp. 12182-12187.

Iwakabe K, et al., "The restraint stress drives a shift in Th1/Th2 balance towards Th2-dominant immunity in mice," *Immunology Letters* (1998) vol. 62, pp. 39-43.

Johnson, A., Daniel, et al., "Effect of heat shock proteins on survival of isolated aortic cells from normal and atherosclerotic cynomolgus macaques," *Atherosclerosis* (1990) vol. 84, pp. 111-119.

Kang, D. H., et al., "TH1 and TH2 cytokine responses to academic stress," *Research in Nursing & Health* (2001) vol. 24, pp. 245-257.

Kansal, R., et al., "Change in colony morphology influences the virulence as well as the biochemical properties pf the *Mycobacterium avium* complex," *Microbial Pathogenesis* (1998) vol. 25, pp. 203-214.

Kim, J.H, et al., "Induction of oral tolerance to Japanese cedar pollen," *Arch Pharm Res* (2001) vol. 24:6, pp. 557-563.

Lawrence, K. D., "Central/peripheral nervous system and immune response," *Toxicology* (2000) vol. 124, pp. 189-201.

Lio, Domenico., et al., "In vitro treatment with interleukin-2 normalizes type-1 cytokine production by lymphocytes from elderly," *Immunopharmacology and Immunotoxicology* (2000) vol. 22:2, pp. 195-203.

Manabe, YC, et al., "Naturally attenuated orally administered *Mycobacterium microti* as a tuberculosis vaccine is better than subcultaneous *Mycobacterium bovis* BCG," *Infection and Immunity* (2002) vol. 70:3 pp. 1566-1570.

Maraveyas, A., et al., "Possible improved survival of patients with stage IV AJCC melanoma receiving SRL 172 immunotherapy: correlation with induction of increased levels of intracellular interleukin-2 in peripheral blood lymphocytes," *Annals of Oncology* (1999) vol. 10 pp. 817-824.

Mehta, S. K., et al., "Epstein-Barr virus reactivation associated with diminished cell-mediated immunity in Antarctic expeditioners," *Journal Medical Virology* (2000) vol. 61 pp. 235-240.

Mukherjee, et al., "Association of antibodies to heat-shock protein-65 with percutanteous tramsluminal coronary angioplasty and subsequent restenosis," *Thrombois and Haemostasis* (1996) vol. 75 pp. 258-260.

Norbiato, G., et al., "Microbial and fungal contamination contributes to physical stress in space flight: studies in the Euromir-95 mission," *J. Garvit Physiol* (1998) vol. 5:1, p. 145-6.

Paik, In-ho, et al., "Psychological stress may induce increased humoral and decreased cellular immunity," *Behavioral Medicine* (2000) vol. 26:3, pp. 139-141.

Prinzis, S., et al., "Search for the molecular basis of morphological varariation in *Mycobacterium avium,*" *Infection and Immunity* (1994) vol. 62:5 pp. 1946-1951.

Sanders, M.E., et al., "Invited review: the scientific basis of *Lactobacillius acidophilus* NCFM functionally as a probiotic," *J. Dairy Sci* (2001) vol. 84:2, pp. 19-31.

Schett, Georg, et al., "Autoantibodies against heat shock protein 60 mediate endothelial cytotoxicity," *J. Clin. Invest* (1995) vol. 96, pp. 2569-2577.

Sharpe, S., et al., "Single oral immunization with replication deficient recombinant adenovirus elicits long-lived transgene-specific cellular and humoral immunal response," *Virology* (2002) vol. 293 pp. 210-216.

Solana, R., et al., "NK and NK/T cells in human senescence," *Vaccine* (2000) vol. 18 pp. 1613-1620.

Stanford, J. L., et al., "Therapeutic vaccination for cancer: the potential value of mycobacterial products," *International Journal of Pharmaceutical Medicine* (1999) vol. 13, pp. 191-195.

Von Hertzen, Leena C., "Maternal stress and T-cell differentiation of the developing immune system: possible implications for the development of asthma andatopy," *J. Allergy Clin. Immunol.* (2002) vol. 109, pp. 923-928.

Wright, Barbara W, et al., "Elevated levels of circulation heat shock protein 70 (Hsp70) in peripheral and renal vascular disease," *Heart Vessels* (2000) vol. 15, pp. 18-22.

Xu, Qingbo, et al., "Induction of arteriosclerosis in normocholesterolemic rabbits by Immunization with heat shock protein 65," *Arteriosclerosis and Thrombosis* (1992) vol. 12:7 pp. 789-799.

Colwell, W., et al., "Potential antileprotic agents. I. Inhibition of a model mycobacterial system by diaryl sulfones," *Journal of Medicinal Chemistry* (1974) vol. 17:1, pp. 142-144.

Girdhar, B. K., et al., "Primary sulphone resistance. A preliminary report," *Leprosy In India* (1978) vol. 50:3 pp. 352-355.

Rightsel, W. A., et al., "Comparative effects of sulfones and rifampin on growth of *Mycobacterium lepraemurium* in macrophage diffusion chamber cultures," *Antimicrobial Agents and Chemotherapy* (1978) vol. 13:3 pp. 509-513.

Tsukamura, M., et al., "Mycobacterium-obuense a rapidly growing scotochromogenic mycobacterium capabale of forming a black product from *p*-aminosalicylate and salicylate," *Journal of General Microbiology* (1971) vol. 68:2, pp. 129-134.

\* cited by examiner

METHOD OF PRODUCING ROUGH STRAINS OF BACTERIA AND USES THEREOF

CLAIM OF PRIORITY

This is a continuation of U.S. patent application Ser. No. 12/086,421, filed Jun. 12, 2008 Oct. 28, 2008, which claims priority under 35 USC 371 to International Application No. PCT/GB2006/004780, filed on Dec. 19, 2006, which claims priority to British Patent Application No. 0526033.6, filed on Dec. 21, 2005, each of which is incorporated by reference in its entirety.

FIELD OF THE INVENTION

The present invention relates to rough strains of bacteria, such as those from the genus *Mycobacterium*. In particular, the present invention relates to methods of obtaining rough strains of bacteria. The present invention yet further relates to a novel *Mycobacterium obuense* rough strain and use of this rough strain of *Mycobacterium obuense*.

BACKGROUND TO THE INVENTION

Methods of obtaining rough strains of bacteria, such as those from the genus *Mycobacterium*, that are known in the art include the plating out of bacteria, such as those from the genus *Mycobacterium*, and looking for any rough colonies. However, any rough strains identified in this way are typically not stable.

Other methods include plating out *Mycobacteria* on medium that contains Tween or glycerol and encouraging pellicle growth. This method has been successful in inducing rough colonies of some species of *Mycobacteria*. However, this method has not been able to induce rough variants in all *Mycobacteria*.

No method to date has been able to induce rough strains of *Mycobacterium obuense*.

Accordingly, there is a need for an improved method that is able to produce rough strains, particularly stable rough strains, of *Mycobacterium*. Such a method could advantageously be used to produce for the first time rough strains of some species of *Mycobacterium* such as *Mycobacterium obuense*.

Advantageously, the present invention has provided such an improved method that has induced for the first time a rough strain, particularly a stable rough strain, of *Mycobacterium obuense*.

Rough strains of fast-growing *Mycobacteria* have a number of advantages:
  stable rough strains do not revert to smooth strains;
  rough strains have a different presentation of antigens and tend to be less virulent in causing disease than smooth strains;
  skin test reagents made from rough strains are more effective than those made from smooth strains;
  rough strains are very effective when used in in vitro cell-mediated immune experiments; and
  the small clumps or particles of several bacilli may be more effective in stimulating phagocytic cells than single organisms of smooth strains.

Furthermore, the present invention has advantageously found that a whole cell of a rough strain of *Mycobacterium obuense* may be used to modulate the immune response of a subject.

Although *M. vaccae* was known to modulate the immune response of a subject—*M. obuense* had never before been considered suitable for use as an immune modulator.

Vaccines and other immune modulators have a major impact in reducing morbidity and mortality from disease. The primary immunity elicited by most current vaccines appears to be mediated by the humoral immune response. For diseases that may require a cellular immune response, such as tuberculosis and leishmaniasis, there are currently no available vaccines that are uniformly effective.

Typically, adjuvants are added to vaccines. The role of the adjuvant is to enhance the body's immune response to specific antigens of the vaccine. Commonly used adjuvants typically produce a humoral immune response but not a cell-mediated immune response. In addition, aluminium adjuvants for example may cause negative side effects, such as sterile abscesses, erythema, swelling, subcutaneous nodules, granulomatous inflammation and contact hypersensitivity.

A vaccine or other immune modulator is sought that modifies a cellular immune response and in particular the T helper cell response, for example, the T helper cell 1 (Th1) and T helper cell 2 (Th2) response.

There are many different autoimmune diseases, and they can each affect the body in different ways. Many of the autoimmune diseases are rare. As a group, however, autoimmune diseases afflict millions of people.

Some autoimmune diseases are known to begin or worsen with certain triggers such as viral, parasitic and chronic bacterial infections. Other less understood influences affect the immune system and the course of autoimmune diseases include ageing, chronic stress, hormones and pregnancy.

Autoimmune diseases are often chronic, requiring lifelong care and monitoring, even when the person may look or feel well. Currently, few autoimmune diseases can be cured or made to go into remission with treatment.

Physicians most often help patients manage the consequences of inflammation caused by the autoimmune disease. In some people, a limited number of immuno-suppressive medications may result in disease remission. However, even if their disease goes into remission, patients are rarely able to discontinue medication. The long-term side effects of immunosuppressive medication can be substantial.

Initiation and progression of vascular injury is a complex, multi-factorial process, but there is growing evidence that inflammatory responses play a key role. Vascular injury is involved in the development of atherosclerosis, and in thrombotic processes that lead to acute ischaemic syndromes such as myocardial infarction, stroke and peripheral artery occlusion.

Immune mechanisms may be important in the development and maintenance of atherosclerosis and myointimal hyperplasia (MIH).

Myointimal Hyperplasia (MIH) can be considered as an exaggerated healing response to injury such as balloon angioplasty. A cascade of events results in: loss of the basement membrane, migration of vascular smooth muscle cells (VSMC) from the media into the intima, VSMC proliferation and phenotypic change to a more secretory fibroblastic cell type and increased production of extracellular matrix, which eventually leads to stenosis or occlusion of the vessel. It occurs after bypass grafting and balloon angioplasty and affects approximately 30% of such cases in clinical practice. It is the major cause of failure of such procedures and treatment of the resulting stenosed and blocked vessels/grafts is problematic. The underlying cellular mechanisms leading to MIH are not well understood and to date no therapy had been developed which can effectively prevent it. The clinical relevance of the current patent relates to the very large numbers of coronary artery angioplasties which are performed annually in the UK and world-wide. Although drug eluting stents are currently producing promising results they are unlikely to prevent restenosis completely. Any safe, relatively inexpensive adjunctive therapy, such as the immunotherapy proposed in this patent, would have a major clinical impact.

The mechanisms involved in immunotherapy against restenosis are complex and not completely elucidated. The endothelial injury caused by angioplasty may be exacerbated by the host immune response to hsp's. Hsp's are proteins produced by stressed cells which have been implicated in the pathogenesis and the pathophysiology of various immunological disorders including atherosclerosis (Xu Q et al. *Arterioscler Thromb* 1992; 12: 789-799). It is likely that they will be present on endothelial and smooth muscle cells in the region of an angioplasty. In effect the hsp acts as an autoantigen which can then be attacked by the immune system. This situation can be induced experimentally by immunising with a cross-reactive *mycobacterial* hsp (hsp65) which leads to endothelial damage in rabbits and mice (Xu Q, et al. *Arterioscler Thromb* 1992; 12: 789-799 and George J, et al. *Circ. Res.* 2000; 86: 1203-1210). The effect appears to be dependent on IL-4 secreted by Th2 lymphocytes, and is probably mediated by antibody George J, et al. *Circ. Res.* 2000; 86: 1203-1210 and Schett G, et al. *J. Clin. Invest.* 1995; 96: 2569-2577). The relevance of these observations to man is suggested by the ability of affinity-purified human antibody eluted from hsp65 columns to damage stressed human endothelial cells in vitro. This finding suggests that the antibody cross-reacts with hsp60 which is the human homologue of hsp65, and may be accessible to antibody when expressed on the membranes of stressed endothelial cells. It has been suggested that such antibodies binding to stressed endothelial cells may be a factor in producing coronary artery disease after heart transplantation (Crisp S J et al. *J Heart Lung Transplant* 1994; 81-91). Mukherjee et al (*Thromb Haemost* 1996; 75: 258-60) showed no association between preoperative antibody levels to hsp65 and coronary restenosis, but did show that those patients where levels of such antibodies dropped after angioplasty were less likely to restenose. In fact the role of antibodies to hsp could be complex, because patients with vascular disease have not only raised antibody, but also raised levels of the hsp themselves (Wright B H, et al *Heart Vessels* 2000; 15: 18-22). Thus an apparent fall in antibody levels may merely reflect an increase in levels of the protein. Moreover the hsp have regulatory effects, and bind to arterial smooth muscle cells, leading to enhanced survival without a requirement for internalisation (Johnson A D et al. *Atherosclerosis* 1990; 84: 111-119).

WO2004/022093 and UK application number 0404102.6 (both of which references are incorporated herein by reference) disclose an immune modulator composition or a pharmaceutical composition comprising a whole cell of a bacterium from the genera *Rhodococcus, Gordonia, Nocardia, Dietzia, Tsukamurella* and *Nocardioides*.

In addition, U.S. application Ser. No. 10/893,524 (incorporated herein by reference) discloses the use of a whole cell of a bacterium from the genera *Rhodococcus, Gordonia, Nocardia, Dietzia, Tsukamurella* and *Nocardioides* in a manufacture of a medicament for the treatment or prevention of post-weaning multisystemic wasting syndrome (PMWS) and/or porcine dermatitis and nephropathy syndrome (PDNS).

However, none of these documents teaches or suggests the use of whole cells of rough strain, preferably a stable rough strain, of *M. obuense* to modulate a cellular immune response.

SUMMARY OF THE INVENTION

The present invention is predicated upon the surprising finding that a rough strain of a bacterium, such as a rough strain of a bacterium from the genus *Mycobacterium*, may be induced by exposure to a sulfone and/or a sulfonamide.

From birth to death the immune system is educated, constantly stimulated and regulated through contact with the environment. Modern urbanisation and public health measures to prevent infectious disease have virtually eliminated this exposure leading to an unprecedented rise in diseases— such as allergies and neoplastic diseases. Restoring the beneficial affects of the environment through the use of killed suspensions of harmless beneficial environmental bacteria may redress the normal balance of the immune system thus acting, therapeutically and/or prophylactically in the treatment of diseases and/or in promoting a healthy immune system.

Thus, in addition or in the alternative, to the method of inducing rough strains of bacteria (such as *Mycobacterium* e.g. *M. obuense*), the present invention is predicated upon the surprising finding that a whole cell of a bacterium from a rough strain of *Mycobacterium obuense* administered to a test subject is particularly effective at eliciting a modification of the immune system, in particular the cellular immune system, of that test subject.

The phrase "cellular immune system", as used herein, includes a cell-mediated immune response which depends upon the presence of T lymphocytes. The term "T lymphocytes" includes cytotoxic T lymphocytes, helper T cells, suppresser T cells and regulatory T cells. Modification of a cell-mediated immune response may be used, for example, to overcome cell-mediated immune disorders including for example an immune system imbalance and immune hypersensitivity.

The terms "modulate", "modify", "modification" and other derivatives thereof, as used herein, mean downregulating, inhibiting, inducing, stimulating, upregulating, altering or otherwise affecting a component or components of the cellular immune system.

The present invention is predicated upon the surprising finding that a whole cell of a rough strain of *Mycobacterium obuense* administered to a test subject is particularly effective at eliciting a modification of the immune system, in particular the cellular immune system of that test subject, which effects a preventative and/or therapeutic effect on autoimmune diseases or autoimmune disorders, particularly those which involve the inflammation of the intima of blood vessels for example.

An advantage of the use of compositions comprising a whole cell of a bacterium from a rough strain of *M. obuense* to effectively treat and/or prevent autoimmune diseases and autoimmune disorders, particularly those which involve the inflammation of the intima of blood vessels for example, may be that this treatment and/or prevention is effected whilst producing fewer long-term side effects than the chemotherapies, i.e. the immunosuppressive medication, now routinely used.

DETAILED ASPECTS OF THE PRESENT INVENTION

In one aspect, the present invention relates to a method of producing a rough strain of a bacterium, said method comprising exposing said bacterium to a sulfone and/or a sulfonamide Suitably, in a method of producing rough strains of a bacterium according to the present invention the rough strain may be isolated.

Preferably, in a method of producing rough strains of a bacterium according to the present invention a bacterium is grown on medium a sulfone and/or a sulfonamide at a concentration of greater than or equal to 5 µg sulfone and/or sulfonamide per 1 ml medium.

Suitably, in a method of producing rough strains of a bacterium according to the present invention said bacterium may be from the genus *Mycobacterium*. Preferably from *Mycobacterium obuense*.

In another aspect, the present invention relates to a rough strain of a bacterium from the genus *Mycobacterium* producible, preferably produced, by a method of the present invention.

In a further aspect, the present invention relates to a rough strain of *Mycobacterium obuense* producible, preferably produced, by a method of the present invention.

In another aspect, the present invention relates to a rough strain of *Mycobacterium obuense* that has been deposited by BioEos Limited of 67 Lakers Rise, Woodmansterne, Surrey, SM7 3LA under the Budapest Treaty on the International Recognition of the Deposit of Microorganisms for the purposes of Patent Procedure at the National Collection of Type Cultures (NCTC), Central Public Health Laboratory, 61 Colindale Avenue, London, NW9 5HT), under Accession Number NCTC 13365 on the 14 Jul. 2005.

In one aspect, the present invention provides an immune modulator composition comprising a whole cell of a rough strain of *Mycobacterium obuense*.

The term "immune modulator", as used herein, means a substance which modulates a cellular immune system of a subject.

The term "whole cell", as used herein, means a bacterium which is intact, or substantially intact. In particular, the term "intact" as used herein means a bacterium which is comprised of all of the components present in a whole cell, particularly a whole, viable cell, and/or a bacterium which has not been specifically treated to remove one or more components from it. By the term "substantially intact" as used herein it is meant that although the isolation and/or purification process used in obtaining the bacterium may result in, for example, a slight modification to the cell and/or in the removal of one or more of the components of the cell, the degree to which such a modification and/or removal occurs is insignificant. In particular, a substantially intact cell according to the present invention has not been specifically treated to remove one or more components from it.

Prior to the present invention the use of whole cells of bacterium from a rough strain of *Mycobacterium obuense* to modulate a cellular immune response was not contemplated. Surprisingly, it has been found that by using a whole cell of a rough strain of *Mycobacterium obuense*, modulation of a cellular immune system can be effected. The modulation of a cellular immune response caused by administration of said whole cell of said rough strain may be advantageously long lasting as compared with the response elicited by administration of an individual component of the bacterium.

Preferably, the composition according to the present invention comprises more than one whole cell, and more preferably comprises a plurality of whole cells.

In a further aspect, the present invention provides an immune modulator composition comprising a whole cell of a bacterium from a rough strain of *Mycobacterium obuense*, which immune modulator composition in use modifies a cellular immune response.

In another aspect, the present invention provides an immune modulator composition comprising an antigen and an adjuvant, wherein said adjuvant comprises a whole cell of a bacterium from a rough strain of *Mycobacterium obuense*

In another aspect, the present invention provides a pharmaceutical composition comprising a whole cell of a bacterium from a rough strain of *Mycobacterium obuense* and optionally a pharmaceutically acceptable carrier, diluent or excipient, which immune modulator composition in use modifies a cellular immune response.

The present invention yet further provides a process of preparation of a pharmaceutical composition of the present invention, said process comprising admixing one or more of the compounds of the present invention with a pharmaceutically acceptable diluent, excipient or carrier.

In a further aspect, the present invention provides an immune modulator composition and/or a pharmaceutical composition comprising a whole cell of a bacterium from a rough strain of *Mycobacterium obuense* and at least one antigen or antigenic determinant.

Suitably, the antigen or antigenic determinant may be an antigen or antigenic determinant from one or more of the following: BCG (bacillus of Calmette and Guerin) vaccine, diphtheria toxoid vaccine, diphtheria/tetanus/pertussis (DTP or Triple) vaccine, pertussis vaccine, tetanus toxoid vaccine, measles vaccine, mumps vaccine, rubella vaccine, OPV (oral poliomyelitis vaccine), *Mycobacterium vaccae*, or part thereof (as taught in GB0025694.1) and a generic *plasmodium* antigen, for example a malaria parasite antigen.

Suitably, the immune modulator composition and/or pharmaceutical composition may comprise two or more such antigens or antigenic determinants.

In another aspect, the present invention provides an immune modulator composition comprising an antigen or an antigenic determinant and an adjuvant, wherein said antigen or antigenic determinant comprises a whole cell of a bacterium from a rough strain of *Mycobacterium obuense*.

When it is the case that whole cell of the bacterium functions as an antigen or antigenic determinant the composition may suitably comprise at least one, preferably at least two, more preferably at least three, further antigens or antigenic determinants.

The present invention further provides the use of an immune modulator composition or a pharmaceutical composition comprising a whole cell of a bacterium from a rough strain of *Mycobacterium obuense*, in the manufacture of a medicament for the treatment or prevention of one or more of: an infection (e.g. a bacterial, viral, for example an infection caused by papilloma viruses, including equine sarcoid, genital warts and dysplasia of the uterine cervix that precedes carcinoma of the cervix, or parasitic infection, for example, malaria, trypanosomiasis, leishmaniasis, infection with *Eimeria* species in poultry and toxoplasmosis) and/or the immunological abnormalities accompanying an infection; an autoimmune disease (e.g. a vascular disorder, such as obliterative vascular disorder, and the immunological aspects underlying myointimal hyperplasia and/or atheroma formation (otherwise known as arteriosclerosis), arthritis and graft rejection.); stress (for example, major trauma stress, psychosocial stress and chronic stress); an allergy (e.g. asthma including allergic asthma, hayfever, allergic dermatitis (eczema), anaphylactic shock, allergies to plant contact or ingestion, stings—such as nettle and insect stings, and allergies to insect bites—such as midges, for instance *Culicoides* (which causes Sweet Itch in horses)); heaves; COPD; PMWS; PDNS; SIPH; cancer (for example melanoma or adenocarcinoma); an immune system imbalance (e.g. an immune system imbalance in children and the elderly); and post-operative stress and infection. An immune system imbalance in the elderly may be referred to as immunosenescence.

The present invention further provides the use of an immune modulator composition or a pharmaceutical composition comprising a whole cell of a bacterium from a rough strain of *Mycobacterium obuense*, in the manufacture of a medicament for the treatment or prevention of one or more viral infections, for example an infection caused by papilloma viruses, including equine sarcoid, genital warts and dysplasia of the uterine cervix that precedes carcinoma of the cervix.

In one aspect, the present invention provides an immune modulator composition and/or a pharmaceutical composition comprising a whole cell of a bacterium from a rough strain of *Mycobacterium obuense*, and at least one antigen or antigenic determinant, wherein said antigen or antigenic determinant is a viral antigen of bovine papilloma viruses.

The present invention further provides the use of an immune modulator composition or a pharmaceutical composition comprising a whole cell of a bacterium from a rough strain of *Mycobacterium obuense*, in the manufacture of a medicament for the treatment or prevention of one or more of a parasitic infection, such as, for example, malaria, trypanosomiasis, leishmaniasis, infection with *Eimeria* species in poultry and toxoplasmosis.

The present invention further provides the use of an immune modulator composition or a pharmaceutical composition comprising a whole cell of a bacterium from a rough strain of *Mycobacterium obuense*, in the manufacture of a medicament for the treatment or prevention of one or more of an autoimmune disease, a vascular disorder, such as an obliterative vascular disorder and the immunological aspects underlying myointimal hyperplasia and/or atheroma formation (otherwise known as arteriosclerosis), arthritis and graft rejection.

The present invention further provides the use of an immune modulator composition or a pharmaceutical composition comprising a whole cell of a bacterium from a rough strain of *Mycobacterium obuense*, in the manufacture of a medicament for the treatment or prevention of stress, such as, for example, major trauma stress, psychosocial stress and/or chronic stress and/or post-operative stress (including the stress related to being administered anaesthetics).

The present invention further provides the use of an immune modulator composition or a pharmaceutical composition comprising a whole cell of a bacterium a rough strain of *Mycobacterium obuense*, in the manufacture of a medicament for the treatment or prevention of one or more of asthma (including allergic asthma), hayfever, allergic dermatitis (eczema), anaphylactic shock, allergies to plant contact or ingestion, stings—such as nettle and insect stings, and allergies to insect bites—such as midges for instance *Culicoides* (which causes Sweet Itch in horses).

Preferably, the immune modulator composition or pharmaceutical composition comprising a whole cell of a bacterium from a rough strain of *Mycobacterium obuense* is used in the manufacture of a medicament for the treatment or prevention of asthma including allergic asthma, and allergies to insect bites—such as midges for instance *Culicoides* (which causes Sweet Itch in horses).

The present invention further provides the use of an immune modulator composition or a pharmaceutical composition comprising a whole cell of a bacterium from a rough strain of *Mycobacterium obuense* in the manufacture of a medicament for the treatment or prevention of one or more of heaves and/or COPD, particularly in horses.

The present invention further provides the use of an immune modulator composition or a pharmaceutical composition comprising a whole cell of a bacterium a rough strain of *Mycobacterium obuense*, in the manufacture of a medicament for the treatment or prevention of one or more of PMWS and/or PDNS.

The present invention further provides the use of an immune modulator composition or a pharmaceutical composition comprising a whole cell of a bacterium from a rough strain of *Mycobacterium obuense*, in the manufacture of a medicament for the treatment or prevention of stress-induced pulmonary haemorrhage (SIPH), preferably exercise-induced pulmonary haemorrhage (EIPH).

The present invention further provides the use of an immune modulator composition or a pharmaceutical composition comprising a whole cell of a bacterium a rough strain of *Mycobacterium obuense*, in the manufacture of a medicament to for the treatment or prevention of melanoma and/or adenocarcinoma.

The present invention further provides the use of an immune modulator composition or a pharmaceutical composition comprising a whole cell of a bacterium a rough strain of *Mycobacterium obuense*, in the manufacture of a medicament for the treatment or prevention of an immune system imbalance in the elderly. Typically, an immune modulator composition or a pharmaceutical composition according to this aspect of the present invention may be an immune enhancer.

The present invention further provides the use of an immune modulator composition or a pharmaceutical composition comprising a whole cell of a bacterium from a rough strain of *Mycobacterium obuense*, in the manufacture of a medicament for enhancing the immune system which may result in for example, enhancement of growth or an increase in the efficiency of feed utilisation. Typically, the immune modulator composition or pharmaceutical composition according to this aspect of the present invention may be an immune enhancer. Advantageously, the immune modulator composition or pharmaceutical composition of the present invention may be used to replace antibiotics that are currently used to promote the growth of livestock. Suitably, the immune modulator composition of the present invention may be used either alone or in combination with other treatments. The term "livestock", as used herein refers to any farmed animal. Preferably, livestock is one or more of horses, poultry, pigs (including piglets), sheep (including lambs), cows or bulls (including calves). More preferably, livestock means pigs—including piglets.

The present invention further provides the use of an immune modulator composition or a pharmaceutical composition comprising a whole cell of a bacterium from a rough strain of *Mycobacterium obuense*, in the manufacture of a medicament for the treatment or prevention of an immune system imbalance in children.

The present invention further provides the use of an immune modulator composition or a pharmaceutical composition comprising a whole cell of a bacterium from a rough strain of *Mycobacterium obuense*, in the manufacture of a medicament for the treatment or prevention of an adverse reaction to childhood vaccines—such as whooping cough vaccinations and the current MMR vaccinations—and/or consequences thereof. The term "adverse reaction", as used herein, means a local or generalised disadvantageous response caused by or primed by the vaccine or the administration thereof, which typically occurs within a short timeframe but which can be delayed (for example by 6-months). An "adverse reaction" may include death of the child. The adverse reaction may be caused as a consequence of a separate event, the response to which has been negatively primed by the vaccine or the administration thereof.

The present invention further provides the use of an immune modulator composition or a pharmaceutical composition comprising a whole cell of a bacterium a rough strain of *Mycobacterium obuense* in the manufacture of a medicament for modifying a cellular immune response.

In a further aspect, the present invention provides an immune modulator composition or a pharmaceutical composition comprising a whole cell of a bacterium from a rough strain of *Mycobacterium obuense* for use as a medicament.

In a further aspect, the present invention provides an immune modulator composition or a pharmaceutical composition comprising a whole cell of a bacterium a rough strain of *Mycobacterium obuense* for use in or as a vaccine.

Suitably, the vaccine may be a prophylactic vaccine or a therapeutic vaccine.

In a further aspect, the present invention provides an immune modulator composition or a pharmaceutical composition comprising a whole cell of a bacterium a rough strain of *Mycobacterium obuense* for use as an immune enhancer.

In a further aspect, the present invention provides an immune modulator composition or a pharmaceutical composition comprising a whole cell of a rough strain of *Mycobacterium obuense* for use in the treatment or prevention of one or more of: an infection (e.g. a bacterial, viral, for example an infection caused by papilloma viruses, including equine sarcoid, genital warts and dysplasia of the uterine cervix that precedes carcinoma of the cervix, or parasitic infection, for example, malaria, trypanosomiasis, leishmaniasis, infection with *Eimeria* species in poultry and toxoplasmosis) and/or the immunological abnormalities accompanying an infection; an autoimmune disease (e.g. a vascular disorder, such as obliterative vascular disorder and the immunological aspects underlying myointimal hyperplasia and/or atheroma formation (otherwise known as arteriosclerosis), arthritis and graft rejection); stress (for example, major trauma stress, psychosocial stress and chronic stress); an allergy (e.g. asthma including allergic asthma, hayfever, allergic dermatitis (eczema), anaphylactic shock, allergies to plant contact or ingestion, stings—such as nettle and insect stings, and allergies to insect bites—such as midges, for instance *Culicoides* (which causes Sweet Itch in horses)); heaves; COPD; PMWS; PDNS; SIPH and cancer (for example melanoma or adenocarcinoma, or virally related cancers such as cervical cancers for example); an immune system imbalance (e.g. an immune system imbalance in children and the elderly) and post-operative stress and post-operative infection.

In a further aspect, the present invention provides an immune modulator composition or a pharmaceutical composition comprising a whole cell of a bacterium a rough strain of *Mycobacterium obuense* for use in the treatment or prevention of a parasitic infection, such as, for example, one or more of malaria, trypanosomiasis, leishmaniasis, infection with *Eimeria* species in poultry and toxoplasmosis.

In a further aspect, the present invention provides an immune modulator composition or a pharmaceutical composition comprising a whole cell of a bacterium from a rough strain of *Mycobacterium obuense* for use in the treatment or prevention of a viral infection, for example an infection caused by papilloma viruses, including equine sarcoid, genital warts and dysplasia of the uterine cervix that precedes carcinoma of the cervix.

In a further aspect, the present invention provides an immune modulator composition or a pharmaceutical composition comprising a whole cell of a bacterium from a rough strain of *Mycobacterium obuense*, for use in the treatment or prevention of one or more of an autoimmune disease, a vascular disorder, such as an obliterative vascular disorder and the immunological aspects underlying myointimal hyperplasia and/or atheroma formation (otherwise known as arteriosclerosis), arthritis and graft rejection.

In a further aspect, the present invention provides an immune modulator composition or a pharmaceutical composition comprising a whole cell of a bacterium a rough strain of *Mycobacterium obuense* for use in the treatment or prevention of stress, such as, for example, one or more of major trauma stress, psychosocial stress and chronic stress, and/or post-operative stress.

In a further aspect, the present invention provides an immune modulator composition or a pharmaceutical composition comprising a whole cell of a bacterium from a rough strain of *Mycobacterium obuense* for use in the treatment or prevention of one or more of asthma (including allergic asthma), hayfever, allergic dermatitis (eczema), anaphylactic shock, allergies to plant contact or ingestion, stings—such as nettle and insect stings, and allergies to insect bites—such as midges for instance *Culicoides* (which causes Sweet Itch in horses). Preferably, the immune modulator composition or a pharmaceutical composition comprising a whole cell of a bacterium from a rough strain of *Mycobacterium obuense* is for use in the treatment or prevention of asthma, including for example allergic asthma, and allergies to insect bites—such as midges, for instance *Culicoides* (which causes Sweet Itch in horses).

In a further aspect, the present invention provides an immune modulator composition or a pharmaceutical composition comprising a whole cell of a bacterium from a rough strain of *Mycobacterium obuense* for use in the treatment or prevention of one or more of heaves and/or COPD, particularly in horses.

In a further aspect, the present invention provides an immune modulator composition or a pharmaceutical composition comprising a whole cell of a bacterium from a rough strain of *Mycobacterium obuense* for use in the treatment or prevention of one or more of PMWS and/or PDNS, particularly in pigs.

In a further aspect, the present invention provides an immune modulator composition or a pharmaceutical composition comprising a whole cell of a bacterium from a rough strain of *Mycobacterium obuense* for use in the treatment or prevention of SIPH, particularly in fish (such as koi) and/or racing animals (such as horses, camels, greyhounds and humans).

In a further aspect, the present invention provides an immune modulator composition or a pharmaceutical composition comprising a whole cell of a bacterium from a rough strain of *Mycobacterium obuense* for use in the treatment or prevention of cancer (for example melanoma and/or adenocarcinoma and/or virally related cancers such as cervical cancer for example).

In a further aspect, the present invention provides an immune modulator composition or a pharmaceutical composition comprising a whole cell of a bacterium from a rough strain of *Mycobacterium obuense* for use in the treatment or prevention of an immune system imbalance, particularly immunosenescence, in the elderly.

In a further aspect, the present invention provides an immune modulator composition or a pharmaceutical composition comprising a whole cell of a bacterium from a rough strain of *Mycobacterium obuense* for use in the treatment or prevention of post-operative infection.

In a further aspect, the present invention provides an immune modulator composition or a pharmaceutical composition comprising a whole cell of a bacterium a rough strain of *Mycobacterium obuense* for use in enhancing the immune system which may result in for example, enhancement of growth or an increase in the efficiency of feed utilisation in, for example, livestock.

In a further aspect, the present invention provides an immune modulator composition or a pharmaceutical composition comprising a whole cell of a bacterium a rough strain of *Mycobacterium obuense* for use in the treatment or prevention of an immune system imbalance in children.

In a further aspect, the present invention provides an immune modulator composition or a pharmaceutical composition comprising a whole cell of a bacterium from a rough strain of *Mycobacterium obuense* for use in the treatment or prevention of an adverse reaction to childhood vaccines—such as whooping cough vaccinations and the current MMR vaccinations—and/or consequences thereof.

In another aspect, the present invention provides the use of a whole cell of a bacterium from a rough strain of *Mycobacterium obuense* in a vaccine or a medicament, wherein said whole cell of said bacterium modifies a cellular immune response.

In one aspect, the whole cell of a rough strain of *Mycobacterium obuense* according to the present invention may downregulate a Th2 response.

In another aspect, the whole cell of a rough strain of *Mycobacterium obuense* according to the present invention may upregulate a Th1 response.

Suitably, the whole cell of a rough strain of *Mycobacterium obuense* according to the present invention may downregulate a Th2 response and upregulate a Th1 response.

Alternatively, the whole cell of a rough strain of *Mycobacterium obuense* according to the present invention may upregulate a Th1 response whilst not affecting a Th2 response.

Alternatively, the whole cell of a rough strain of *Mycobacterium obuense* according to the present invention may downregulate a Th2 response, whilst also downregulating a Th1 response.

Alternatively, the whole cell of a rough strain of *Mycobacterium obuense* according to the present invention may upregulate a Th2 response, whilst also upregulating a Th1 response.

In another aspect, the present invention provides a method for treating or preventing a condition in a subject comprising administering an effective amount of a pharmaceutical composition and/or immune modulator composition to a subject wherein the said composition modulates a cellular immune response.

Suitably the effective amount of the pharmaceutical composition and/or immune modulator composition may be administered as a single dose. Alternatively, the effective amount of the pharmaceutical composition and/or immune modulator composition may be administered in multiple (repeat) doses, for example two or more, three or more, four or more, five or more, ten or more, or twenty or more repeat doses.

In a further aspect, the present invention provides a method for immunising a subject comprising administering a pharmaceutical composition and/or immune modulator composition according to the present invention to a subject.

In a further aspect of the present invention, there is provided a method for protecting, including immunising, a subject comprising administering a pharmaceutical composition and/or immune modulator composition according to the present invention.

Preferably, a subject is protected, for example is immunised, against one or more of: an infection (e.g. a bacterial, viral, for example an infection caused by papilloma viruses, including equine sarcoid, genital warts and dysplasia of the uterine cervix that precedes carcinoma of the cervix, or parasitic infection, for example, malaria, trypanosomiasis, leishmaniasis, infection with *Eimeria* species in poultry and toxoplasmosis) and/or the immunological abnormalities accompanying an infection; an autoimmune disease (e.g. a vascular disorder, such as obliterative vascular disorder and the immunological aspects underlying myointimal hyperplasia and/or atheroma formation (otherwise known as arteriosclerosis), arthritis and graft rejection); stress (for example, major trauma stress, psychosocial stress and chronic stress); an allergy (e.g. asthma including allergic asthma, hayfever, allergic dermatitis (eczema), anaphylactic shock, allergies to plant contact or ingestion, stings—such as nettle and insect stings, and allergies to insect bites—such as midges, for instance *Culicoides* (which causes Sweet Itch in horses)); heaves; COPD; PMWS; PDNS; cancer (for example melanoma or adenocarcinoma or virally related cancers, such as cervical cancer); an immune system imbalance (e.g. an immune system imbalance in children and the elderly); and post-operative stress and post-operative infection.

Preferably, a subject is immunised against one or more of malaria, trypanosomiasis, leishmaniasis, infection with *Eimeria* species in poultry and toxoplasmosis.

Preferably, a subject is immunised against viral infections, for example against papilloma virus infections, including against equine sarcoid, genital warts or dysplasia of the uterine cervix that precedes carcinoma of the cervix.

Preferably, a subject is immunised against one or more of an autoimmune disease, a vascular disorder, such as an obliterative vascular disorder and the immunological aspects underlying myointimal hyperplasia and/or atheroma formation (otherwise known as arteriosclerosis), arthritis and graft rejection.

Preferably, a subject is protected against stress, such as, for example, one or more of major trauma stress, psychosocial stress and chronic stress and/or post-operative stress.

Preferably, a subject is protected (including immunised) against one or more of asthma (including allergic asthma), hayfever, allergic dermatitis (eczema), anaphylactic shock, allergies to plant contact or ingestion, stings—such as nettle and insect stings, and allergies to insect bites—such as midges for instance *Culicoides* (which causes Sweet Itch in horses). More preferably, a subject is immunised against asthma including for example allergic asthma, and allergies to insect bites—such as midges, for instance *Culicoides* (which causes Sweet Itch in horses.

Preferably, a subject is protected (including immunised) against one or more of COPD and/or heaves, particularly wherein the subject in a horse.

Preferably, a subject is protected (including immunised) against one or more of PMWS and/or PDNS, particularly wherein the subject in a pig.

Preferably, a subject is protected (including immunised) against SIPH, particularly wherein the subject in a fish (such as koi), including EIPH, particularly wherein the subject is a racing animal (such as a human, horse, camel or greyhound).

Preferably, a subject is protected (including immunised) against post-operative stress and infection.

Preferably, a subject is protected against the development and/or the progression of a cancer, for example melanoma and/or adenocarcinoma and/or virally related cancers such as cervical cancers for example.

Preferably, a subject is protected (including immunised) against an immune system imbalance in the elderly. In particular, the composition according to the present invention may be used to regulate the subject's immune system.

Preferably, a subject is protected (including immunised) against an immune system imbalance in children. In particular, the composition according to the present invention may be used to regulate the subject's immune system, particularly the child's immune system.

Preferably, a subject is protected (including immunised) against an adverse reaction to childhood vaccines and/or consequences thereof. In particular, the immune system of the subject is regulated, particularly a child's immune system, before and/or during and/or after administration of the childhood vaccine.

The term "protected" as used herein means that the subject is less susceptible to the disease/disorder as compared with a subject not treated or administered with the compositions according to the present invention and/or that the subject is more able to counter or overcome the disease/disorder as compared with a subject not treated or administered with the compositions according to the present invention.

In another aspect, the present invention provides administering an effective amount of a pharmaceutical composition and/or an immune modulator composition according to the present invention to a subject, wherein said composition is co-administered with an antigen or antigenic determinant.

When the composition is co-administered with an antigen or antigenic determinant in accordance with the present invention the antigen or antigenic determinant may suitably be an antigen or antigenic determinant from one or more of the following: BCG (bacillus of Calmette and Guerin) vaccine, diphtheria toxoid vaccine, diphtheria/tetanus/pertussis (DTP or Triple) vaccine, pertussis vaccine, tetanus toxoid vaccine, measles vaccine, mumps vaccine, rubella vaccine, OPV (oral poliomyelitis vaccine), *Mycobacterium vaccae*, or part thereof (as taught in GB0025694.1) and a generic *plasmodium* antigen, for example a malaria parasite antigen. Suitably two or more, or three or more, of such antigens or antigenic determinants may be co-administered with a pharmaceutical composition or an immune modulator composition according to the present invention.

Preferably, a medicament according to the present invention is used for the treatment or prevention of one or more of: an infection (e.g. a bacterial, viral, for example an infection caused by papilloma viruses, including equine sarcoid, genital warts and dysplasia of the uterine cervix that precedes carcinoma of the cervix, or parasitic infection, for example, malaria, trypanosomiasis, leishmaniasis, infection with *Eimeria* species in poultry and toxoplasmosis) and/or the immunological abnormalities accompanying an infection; an autoimmune disease (e.g. a vascular disorder, such as obliterative vascular disorder, arthritis and graft rejection); stress (for example, major trauma stress, psychosocial stress and chronic stress; an allergy (e.g. asthma including allergic asthma, hayfever, allergic dermatitis (eczema), anaphylactic shock, allergies to plant contact or ingestion, stings—such as nettle and insect stings, and allergies to insect bites—such as midges, for instance *Culicoides* (which causes Sweet Itch in horses)); heaves; COPD; PMWS; PDNS; SIPH and cancer (for example melanoma or adenocarcinoma or a virally related cancer such as cervical cancers for example); an immune system imbalance (e.g. an immune system imbalance in children and the elderly); and post-operative stress and post-operative infection.

Preferably, a medicament according to the present invention is used for the treatment or prevention of one or more of malaria, trypanosomiasis, leishmaniasis, infection with *Eimeria* species in poultry and toxoplasmosis.

Preferably, a medicament according to the present invention is used for the treatment or prevention of viral infections, for example papilloma virus infections, including equine sarcoid, genital warts or dysplasia of the uterine cervix that precedes carcinoma of the cervix for example.

Preferably, a medicament according to the present invention is used for the treatment or prevention of one or more of an autoimmune disease, an obliterative vascular disorder and the immunological aspects underlying myointimal hyperplasia and/or atheroma formation (otherwise known as arteriosclerosis), arthritis and graft rejection.

Preferably, a medicament according to the present invention is used for the treatment or prevention of stress, such as, for example, major trauma stress, psychosocial stress and chronic stress.

Preferably, a medicament according to the present invention is used for the treatment or prevention of one or more of asthma (including allergic asthma), hayfever, allergic dermatitis (eczema), anaphylactic shock, allergies to plant contact or ingestion, stings—such as nettle and insect stings, and allergies to insect bites—such as midges, for instance *Culicoides* (which causes Sweet Itch in horses). More preferably, a medicament according to the present invention is used for the treatment or prevention of asthma, including allergic asthma, and allergies to insect bites—such as midges, for instance *Culicoides* (which causes Sweet Itch in horses).

Preferably, a medicament according to the present invention is used for the treatment or prevention of one or more of COPD and heaves.

Preferably, a medicament according to the present invention is used for the treatment or prevention of one or more of PMWS and PDNS.

Preferably, a medicament according to the present invention is used for the treatment or prevention of SIPH.

Preferably, a medicament according to the present invention is used for the treatment or prevention of cancers (for example melanoma and/or adenocarcinoma and/or virally related cancers such as cervical cancers for example).

Preferably, a medicament according to the present invention is used for the treatment or prevention of an immune system imbalance in the elderly.

Preferably, a medicament according to the present invention is used for the treatment or prevention of post-operative stress or infection.

Preferably, a medicament according to the present invention is used for the treatment or prevention of an immune system imbalance in children.

Preferably, a medicament according to the present invention is used for the treatment or prevention of an adverse reaction to childhood vaccines and/or consequences thereof.

In a further aspect of the present invention, a pharmaceutical composition or an immune modulator composition according to the present invention may comprise bacteria from a rough strain of *Mycobacterium obuense*. Suitably, the composition may comprise two or more, or three or more, bacteria from a rough strain of *Mycobacterium obuense*.

Suitably, the bacterium for use in accordance with the present invention may be used in conjunction with other immune enhancing bacteria such as bacteria from any of the following genera *Rhodococcus, Gordonia, Nocardia, Dietzia, Tsukamurella* and *Nocardioides* including any species from any of these genera such as, *Gordonia bronchialis, G. amarae, G. sputti, G. terrae, Nocardia asteroides, Dietzia maris, Tsukamurella paurometabola, Rhodococcus ruber,*

*Rhodococcus rhodnii, R. coprophilus, Nocardioides albus* and *Tsukamurella inchonensis* for example.

Suitably, the species used from each particular genus are ones which can be grown on medium, which is a low, preferably non-, antigenic medium. By way of example only, a suitable non-antigenic medium is Sauton's medium.

More preferably, bacteria to be used in conjunction with the bacteria for use in accordance with the present invention are from the genus *Rhodococcus*. including *Rhodococcus ruber* (previously known as *Nocardia rubra*), *Rhodococcus rhodocrous, Rhodococcus rhodnii, Rhodococcus coprophilus, Rhodococcus opacus, Rhodococcus erythopolis*.

More preferably, a bacterium to be used in conjunction with the bacteria for use in accordance with the present invention is *Rhodococcus ruber*.

By way of example only, one or more of the organisms *Gordonia bronchialis, Rhodococcus ruber, Rhodococcus rhodocrous, Rhodococcus rhodnii, Dietzia maris* and *Gordonia terrae* in conjunction with the bacteria for use in the present invention may be effective in the treatment and/or prevention of parasitic infections.

By way of example only, one or more of the organisms *Tsukamurella inchonensis, Gordonia amarae* and *Nocardia asteroids* in conjunction with the bacteria for use in the present invention may be particularly effective in the treatment and/or prevention of allergies, such as allergies to insect bites—such as midges for example, and/or the treatment and/or prevention of cancers, including skin neoplasms such as Equine sarcoid.

By way of example only, *Rhodococcus coprophilus* in conjunction with the bacteria for use in the present invention may be particularly effective in the modulation of infections, in particular parasitic infections, and/or enhancing growth in livestock.

In one embodiment of the present invention whole cells of a bacterium from may be used in conjunction with *Rhodococcus coprophilus* in the prevention or treatment of PMWS and/or PDNS.

In one embodiment of the present invention whole cells of a bacterium from a rough strain of *Mycobacterium obuense* may be used in conjunction with *Tsukamurella inchonensis* in the prevention or treatment of SIPH.

Preferably, the bacterium according to the present invention is killed prior to use.

Preferably, the bacterium according to the present invention is killed by heat-treatment thereof, for example, heat-treatment in an autoclave at 121° C. for 15 minutes. Other suitable treatments for killing the bacterium may include ultraviolet or ionising radiation or treatment with chemicals such as phenol, alcohol or formalin. Suitably, the ionising radiation may be carried out by exposure to 2.5 Mrads from a $Co_{60}$ source.

Preferably, the bacterium according to the present invention is purified and/or isolated.

Preferably, the bacterium according to the present invention is suspended in water or buffered saline, suitably borate buffered at pH 8.

The term "subject", as used herein, means an animal. Preferably, the subject is a mammal, bird, fish or crustacean including for example livestock and humans. In some aspects of the present invention, the subject may suitably be a human.

In an aspect of the present invention, for example in the treatment of PMWS and/or PDNS, the subject may be a pig.

In another aspect of the present invention, for example in the treatment of COPD, heaves and/or *Culicoides*, the subject may be a horse.

In another aspect of the present invention, for example in the treatment of SIPH, the subject may be a fish (such as koi) or a racing animal (such as a human, horse, camel or greyhound). Preferably the subject is a racing animal.

The term "immune modulator" as used herein includes a vaccine.

In some embodiments of the present invention, the term "rough strain" refers to a stable rough strain. By "stable" it is meant that a rough strain retains it rough colonial morphology for greater than or equal to 20 successional cultures.

The term "colonial morphology" or "colony morphology" as used herein means the cultural characteristics of a bacterium on an agar plate.

The term "rough" as used herein means other than smooth. The term "rough" as used herein may include characteristics such as an irregular colony morphology, and may include for instance undulate and/or lobate morphology.

In another embodiment of the present invention, the term "rough" as used herein means that the strain is unable and/or substantially unable to produce O-polysaccharide.

Producing Rough Strains

Some aspects of the present invention relate to methods of producing a rough stain of bacteria by exposing bacteria to a sulfone and/or a sulfonamide or the use of a sulfone and/or a sulfonamide to produce rough strains.

Such methods and uses are predicated on the surprising finding that exposure of a bacterium (such as a smooth variant of *Mycobacterium*) a sulfone and/or a sulfonamide results in the production of rough variants.

Preferably, a bacterium for use in a method of the present invention is from a genus of aerobic organisms in the order of Actinomycetales. Preferably, said bacterium is from the genus *Mycobacterium*. Suitably, said bacterium is from *Mycobacterium obuense*.

Suitably, a bacterium for use in the method of the present invention may be grown on any suitable medium, such as Middlebrook 7H11 medium.

Preferably a bacterium for use in the present invention is exposed to a concentration of a sulfone and/or a sulfonamide at a concentration of greater than or equal to a sulfone and/or a sulfonamide per 1 ml medium. Preferably at a concentration of greater than or equal to 7.5 μm/ml. Preferably at a concentration of greater than or equal to 10 μg/ml. Preferably at a concentration of less than 30 μg/ml. Preferably at a concentration or equal to or less than 20 μg/ml. Preferably at about 12 μg/ml.

Suitably, a sulfone and/or a sulfonamide may be admixed with a suitable medium and a bacterium may be grown thereon.

Rough colonies of a bacterium produced by a method of the present invention may further be isolated.

Suitably, rough colonies of a bacterium produced by a method of the present invention may be stable.

In some embodiments of the present invention the term "rough strain" refers to a strain of bacteria that is able to retain a rough morphology on at least 3 repeated cultures in the absence of sulfone and/or sulfonamide thereof.

Sulfone

The term sulfone refers to a compound of the formula (I):

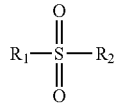

(I)

wherein $R_1$ is a hydrocarbyl group, $R_2$ is a hydrocarbyl group.

Preferably, $R_1$ is selected from an alkyl, a substituted alkyl, an aryl, a substituted aryl, a heteroaryl and a substituted heteroaryl group.

Preferably, $R_1$ is selected from an aryl, a substituted aryl, a heteroaryl and a substituted heteroaryl group.

Preferably, $R_1$ is a substituted phenyl group.

Preferably, $R_1$ is a 4-amino-phenyl group.

Preferably, $R_2$ is selected from an alkyl, a substituted alkyl, an aryl, a substituted aryl, a heteroaryl and a substituted heteroaryl group.

Preferably, $R_2$ is selected from an aryl, a substituted aryl, a heteroaryl and a substituted heteroaryl group.

Preferably, $R_2$ is a substituted phenyl group.

Preferably, $R_2$ is a 4-amino-phenyl group.

$R_1$ and $R_2$ may be the same or different.

In one preferred embodiment, the sulfone is 4,4'-diaminodiphenyl sulfone and/or an analogue thereof.

4,4'-Diaminodiphenyl sulfone is commonly marketed by Sigma under the trade mark Dapsone™.

Synonyms for 4,4'-Diaminodiphenyl sulfone include N,N'-Diphenyl sulfondiamide; 4,4'-Sulfonyldianiline; Di(p-aminophenyl)sulfone; Novophone; Diaphenylsulfon; Dumitone; Diphone; 4-Aminophenyl sulfone; Bis(p-aminophenyl)sulfone; WR 448; F 1358; Croysulfone; Diphenasone; Metabolite C; Dapsone (USAN); 1,1'-Sulfonylbis[4-aminobenzene]; Diaminodiphenyl sulfone; Di(4-aminophenyl)sulfone; p,p'-Sulfonyldianiline; Bis(4-aminophenyl)sulfone; 4,4'-Sulfonylbisbenzamine; Eporal; DADPS; diaphenylsulfone; dapsone; Avlosulfon; Benzenamine, 4,4'-sulfonylbis-; Aniline, 4,4'-sulfonyldi-; Udolac; DDS, pharmaceutical; DSS; DDS; p,p'-Diaminodiphenyl sulfone; Sulfadione; Disulone; Avlosulfone; p-Aminophenyl sulfone; Dapson; Sulfona; NSC 6091D; and Diaminodiphenylsulfone.

The term "Dapsone™" as used herein refers to N,N'-Diphenyl sulfondiamide and relates to any compound that has the following formula:

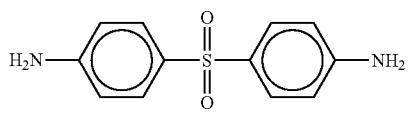

Sulfonamide

The term sulfonamide refers to a compound of the formula (II):

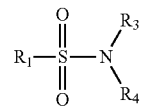

(II)

wherein $R_1$ is a hydrocarbyl group, $R_3$ is a hydrogen or a hydrocarbyl group, $R_4$ is a hydrogen or a hydrocarbyl group.

Preferably, $R_1$ is selected from an alkyl, a substituted alkyl, an aryl, a substituted aryl, a heteroaryl and a substituted heteroaryl group.

Preferably, $R_1$ is selected from an aryl, a substituted aryl, a heteroaryl and a substituted heteroaryl group.

Preferably, $R_1$ is a substituted phenyl group.

Preferably, $R_1$ is a 4-amino-phenyl group.

Preferably, $R_3$ is selected from hydrogen, an alkyl, a substituted alkyl, an aryl, a substituted aryl, a heteroaryl and a substituted heteroaryl group.

Preferably, $R_3$ is selected from an aryl, a substituted aryl, a heteroaryl and a substituted heteroaryl group.

Preferably, $R_3$ is a substituted phenyl group.

Preferably, $R_3$ is a 4-amino-phenyl group.

Preferably, $R_4$ is selected from hydrogen, an alkyl, a substituted alkyl, an aryl, a substituted aryl, a heteroaryl and a substituted heteroaryl group.

In one embodiment, at least one of $R_3$ and $R_4$ is hydrogen.

In another embodiment, at least one of $R_3$ and $R_4$ is an alkyl or a substituted alkyl group.

DEFINITIONS

The term "hydrocarbyl group" as used herein means a group comprising at least C and H and may optionally comprise one or more other suitable substituents. Examples of such substituents may include halo-, alkoxy-, nitro-, an amino group, a hydrocarbon group, an N-acyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen.

In one preferred embodiment of the present invention, the hydrocarbyl group is selected from an alkyl, a substituted alkyl, an aryl, a substituted aryl, a heteroaryl and a substituted heteroaryl group.

The term "alkyl" refers to straight chain, branched chain or cyclic hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, etc. Lower alkyl groups, that is, alkyl groups of 1 to 6 carbon atoms, are most preferred.

The term "substituted alkyl" refers to alkyl groups substituted with one, two or three groups selected from halogen, nitro, cyano, hydroxy, haloalkyl, haloalkoxy, —$OR_x$, —$NR_xR_y$, —$SR_x$, —$C(=O)R_x$, —$OC(=O)R_x$, —$S(=O)R_x$, —SO$_2$R$_x$, —SO$_3$R$_x$, —CO$_2$R$_x$, —NR$_x$C(=O)R$_y$, —NR$_x$CO$_2$R$_y$, —NR$_x$SO$_2$R$_y$, —SO$_2$NR$_x$R$_y$, or —C(=O)NR$_x$R$_y$, wherein the or each R$_x$ is independently selected from hydrogen, C$_{1-6}$alkyl, C$_{2-6}$alkenyl, aryl, heteroaryl and benzyl; wherein the or each R$_y$ is independently selected from hydrogen, C$_{1-6}$alkyl, C$_{2-6}$alkenyl, aryl, heteroaryl and benzyl.

The term "aryl" refers to phenyl, 1-naphthyl and 2-naphthyl, with phenyl being preferred, as well as such rings having fused thereto a cycloalkyl, cycloalkenyl, heterocyclo, or heteroaryl ring.

The term "heteroaryl" refers to aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. Examples of heteroaryl rings include, without limitation: furan, thiophene, pyrrole, oxazole, thiazole, imidazole, isoxazole, pyrazole, isothiazole and pyridine.

The term "heteroatoms" shall include oxygen, sulfur and nitrogen.

The terms "substituted aryl" and "substituted heteroaryl" includes such rings having one, two or three suitable substituents.

The term "analogues of 4,4'-diaminodiphenyl sulfone" means a compound with the basic structure of 4,4'-diaminodiphenyl sulfone wherein from one to six of the hydrogen atoms and/or amino groups attached to the phenyl rings have been substituted with a suitable substituent, and no more that three suitable substituents appear on either of the phenyl rings. Suitable substituents for analogues of 4,4'-diaminodiphenyl sulfone may include substituting an amino group with a hydrogen.

Preferably the or each suitable substituent is selected from C$_{1-6}$alkyl, C$_{2-6}$alkenyl, phenyl, benzyl, halogen, nitro, cyano, hydroxy, haloalkyl, haloalkoxy, —OR$_x$, —NR$_x$R$_y$, —SR$_x$, —C(=O)R$_x$, —OC(=O)R$_x$, —S(=O)R$_x$, —SO$_2$R$_x$, —SO$_3$R$_x$, —CO$_2$R$_x$, —NR$_x$(=O)R$_y$, —NR$_x$CO$_2$R$_y$, —NR$_x$SO$_2$R$_y$, —SO$_2$NR$_x$R$_y$, or —C(=O)NR$_x$R$_y$, wherein the or each R$_x$ is independently selected from hydrogen, C$_{1-6}$alkyl, C$_{2-6}$alkenyl, aryl, heteroaryl and benzyl; wherein the or each R$_y$ is independently selected from hydrogen, C$_{1-6}$alkyl, C$_{2-6}$alkenyl, aryl, heteroaryl and benzyl.

Preferably the or each suitable substituent is —NR$_x$R$_y$, wherein R$_x$ and R$_y$ are as defined above.

Preferably, the or each suitable substituent is —NH$_2$.

When a subscript is used in conjunction with a group such as C$_{1-4}$alkyl, the subscript refers to the number of carbon atoms that the group will contain, in addition to heteroatoms. Thus, the term hydroxyC$_{1-4}$alkyl or C$_{1-4}$hydroxyalkyl refers to an alkyl group of one to four carbon atoms having an OH substituent on one of the carbon atoms.

The term "alkenyl" refers to straight chain, branched chain or cyclic hydrocarbon groups having at least one double bond. Alkenyl groups of 2 to 6 carbon atoms and having one double bond are most preferred.

The term "halo" or "halogen" refers to chloro, bromo, fluoro and iodo.

The term "haloalkyl" means an alkyl having one or more halo substituents. Thus, it includes, for example, trifluoromethyl. The term "perfluoromethyl" means a methyl group having two or three fluoro substituents.

The term "haloalkoxy" means an alkoxy group having one or more halo substituents. For example, "haloalkoxy" includes —OCF$_3$.

Therapeutic Uses

The immune modulators of the present invention may be used in therapy. In particular such compounds may be used to modulate T lymphocyte responses in vivo and/or other cells involved in an immune response in vivo.

Immune modulator/pharmaceutical compositions capable of modulating, in particular blocking, T cell proliferation and/or differentiation and/or activity may be used against any disorder which is susceptible to prevention or treatment by the modulation of an adaptive immune response, i.e. a cellular immune response.

Suitably, the compositions according to the present invention are used to modulate a cellular immune response to treat or prevent one or more of: an infectious disease (such as a bacterial infection e.g. methycillin-resistant *Staphylococcus aureus*, tuberculosis, including multidrug resistant tuberculosis and leprosy; chronic viral infections, for example hepatitis, HIV and infections caused by papilloma viruses, including equine sarcoid, genital warts and dysplasia of the uterine cervix that precedes carcinoma of the cervix; latent viral infections, such as shingles (Herpes zoster) or cold sores (Herpes simplex) for example; or parasitic infections, for example malaria, trypanosomiasis, leishmaniasis, infection with *Eimeria* species in poultry and toxoplasmosis); an allergy (such as allergic dermatitis or allergic asthma); an autoimmune disease (e.g. a vascular disorder, such as obliterative vascular disorder, arthritis and graft rejection); stress (such as major trauma stress, psychosocial stress and chronic stress); PMWS, PDNS, SIPH and cancer (for example, the composition may be administered regularly throughout adult life to counter the effects of tobacco).

A more extensive list of disorders is given in WO-A-98/09985. For ease of reference, part of that list is now provided: inflammation associated with hypersensitivity, allergic reactions, asthma, inflammation associated with aphthus ulceration, ulcerative colitis, hepatic fibrosis, liver cirrhosis or other hepatic diseases, dermatitis, in particular atopic dermatitis e.g. eczema, periodontal diseases or other dental diseases, to treat or ameliorate monocyte or leukocyte proliferative diseases, e.g. leukaemia, other cancers.

Infectious Diseases

Compositions capable of modulating, in particular stimulating (i.e. inducing or enhancing) T cell proliferation and/or differentiation or of preventing the induction of or reversing T cell anergy may be used generally to boost or induce T cell immune responses. Virtually all adaptive immune responses require the activation of T cells and their differentiation into cytokine-producing cells. Thus, these compositions may be used generally to prevent and/or treat infectious diseases— such as viral or bacterial. Suitably, these compositions may be used to prevent and treat parasitic infections, e.g. malaria, leishmaniasis, toxoplasmosis and trypanosomiasis). Suitably, these compositions may be used to prevent or treat viral infections, for example infections caused by papilloma viruses, including equine sarcoid, genital warts and dysplasia of the uterine cervix that precedes carcinoma of the cervix.

In one aspect of the present invention the infection is preferably trypanosomiasis.

In another aspect of the present invention the infection is preferably one caused by papilloma viruses, particularly bovine papilloma viruses 1 and 2. In a further aspect of the present invention the infection is preferably one or more of equine sarcoid, genital warts and dysplasia of the uterine cervix that precedes carcinoma of the cervix.

Equine Sarcoid

The compositions of the present invention may also be used to prevent and treat equine sarcoid.

Equine sarcoid is the commonest skin neoplasm of horses and is associated with infection with bovine papilloma viruses 1 and 2 (Chambers et al J. Gen. Virol. 2003: 84: 1055-1062). This condition is currently without an effective treatment, although surgery, non-specific immune treatment and cytotoxic drugs may all have some effect.

The compositions of the present invention are preferably administered in the same lymph node drainage area as a lesion or neoplasm.

PMWS and PDNS

Post-weaning multisystemic wasting syndrome (PMWS) affects piglets post-weaning from 4 to 16 weeks of age (15-50 kg). Typically PMWS affects piglets one to two weeks after weaning and is very different from the wasting/poor wearer who fails to eat or drink adequately after weaning. PMWS piglets are weaners which have started to grow and then collapse quickly and often have an extremely poor response to antibiotics.

Porcine dermatitis and nephropathy syndrome (PDNS) affects pigs from 8 to 18 weeks of age and the most obvious signs are red-purple blotches on the skin, which become brown and crusted after a few days. Pigs are lethargic and may have swollen legs resulting from their nephropathy. This syndrome, also, responds poorly to antibiotics.

The causal agents of both PMWS and PDNS are at present unknown. The most likely suspect in both syndromes is a pig circovirus "type II" which is antigenically distinct from widely distributed normal non-pathogenic pig circovirus "type I". Circovirus II (PCV II) has been identified on UK farms serologically. PDNS, which is thought to be an immune complex mediated disease, may also involve bacteria in its aetiology, though the part that they play is not clear Suitably the compositions of the present invention may be used in the manufacture of a medicament for the treatment or prevention of PMWS and/or PDNS.

SIPH

The compositions of the present invention may also be used to prevent and treat SIPH. invention may also be used to treat high-altitude pulmonary edema (HAPE). Stress-induced pulmonary haemorrhage (SIPH) is a condition that causes bleeding from blood vessels within the lung when the animal is stressed. The term "SIPH" as used herein may encompass the condition HAPE (high altitude pulmonary edema), which is a condition caused by stress-failure of the pulmonary capillaries allowing fluid uptake into the lung (also known as wet-lung). In addition, the term "SIPH" as used herein may also encompasses exercise-induced pulmonary haemorrhage (EIPH), which is a condition that causes bleeding from blood vessels within the lung during strenuous exercise.

HAPE is a potentially fatal condition that typically occurs 2 to 4 days after ascent to altitudes above 3000 m. With usual ascent rates, the incidence is about 1% to 2%, but as many as 10% of people ascending rapidly to 4500 m may develop the condition. HAPE may be preceded by acute mountain sickness, but this is not always the case. The predominant symptom is dyspnea with reduced exercise tolerance. There is often a dry cough at first, but this may progress to a cough that produces frothy, blood stained sputum. Tachypnea and tachycardia are common on examination.

EIPH is known to affect mammals, particularly racing mammals, such as horses, greyhounds, camels and humans. EIPH is known to affect mammals, particularly racing mammals, after intense exercise.

EIPH is most widely described in thoroughbred horses, where it is thought to cause a loss of performance, but has also been observed in standardbred racing (trotting or pacing), polo, show jumping, cross country and barrel racing horses. EIPH is a common condition it is believed afflicting up to 85% of equine athletes.

The symptoms of EIPH vary from minor bleeding detected by observing red blood cells in broncho-alveolar fluid obtained by fibroscopy, to blood appearing in mucus froth around the nostrils at the end of a race. Although in the most severe cases, EIPH manifests as bleeding from the nostrils (epistaxis) but many horses do not show any signs. The use of endoscopy has shown that 40-75% of thoroughbred horses do have blood in their trachea after racing Diagnosis can also be achieved by tracheal washing and by bronchoalveolar lavage (BAL).

Allergy

The compositions of the present invention may also be used to prevent and treat allergies (e.g. asthma including allergic asthma, hayfever, allergic dermatitis (eczema), anaphylactic shock, allergies to plant contact or ingestion, stings—such as nettle and insect stings, and allergies to insect bites—such as midges for instance *Culicoides* (which causes Sweet Itch in horses).

Sweet Itch is one of the commonest skin diseases seen in horses, particularly in wild horses and/or ponies. About 3% of horses in the U.K. are affected to some degree. Most horses show signs between 1 and 4 years of age and the condition generally worsens during summer. Certain breeds are particularly prone to the disease. Shires, Hackneys and Welsh and Icelandic ponies have all been suggested as susceptible breeds. Sweet Itch is caused by hypersensitivity to the bites of the tiny fly *Culicoides*. In the UK, the fly is present from April to October but peaks in numbers in May to September. The flies feed on the horse at specific sites usually around the tail head and under the mane. There are 20 species of *Culicoides* present in the UK and some feed underneath the horses' abdomen.

By way of example only, the compositions of the present invention may also be used to prevent and/or treat anaphylactic shock by administering a subject, which subject has a predisposition to suffer from anaphylactic shock (for instance a subject who is known to have an allergy, such as an allergy to peanuts for instance) with a composition according to the present invention, thus to reduce the subject's predisposition to anaphylactic shock should they (accidentally) come into contact with the antigen, e.g. peanuts for instance, towards which they may react adversely.

Heaves/COPD

The compositions of the present invention may also be used to prevent and treat heaves and/or COPD (Chronic Obstructive Pulmonary Disease).

Heaves is an equine lung disease with similarities to human asthma and COPD. The clinical signs in the horse are initiated by an allergic response to the particles in hay dust in lungs already damaged with a degree of fibrosis. It is most often seen in older horses (greater than six years old) that are stabled during the winter months. Hay contains microorganisms—such as bacteria and fungi as well as tiny particles of feed grains, plants, faeces, dander, and pollen. These tiny particles become aerosolised in hay dust and elicit an allergic response and fibrosis when they are inhaled by horses with heaves. The primary microorganisms believed to be involved in the etiology of heaves are Aspergillus fumigatus, Thermoactinomyces vulgaris and Faenia rectivirgula. Both reduction of the bronchospasm of asthma and the fibrosis of COPD are within the scope of the patent.

Autoimmune Diseases

The compositions of the present invention may be used to treat and/or prevent an autoimmune disease mechanistically related to poor T cell regulation and/or T cell dysregulation. Examples of autoimmune diseases include one or more of the following: unwanted immune reactions and inflammation including arthritis, including rheumatoid arthritis, psoriasis, psoriatic arthropathy, vascular disorders, in particular a vascular disorder in which there is inflammation of the intima of the blood vessel, examples of vascular disorders are atheroma formation (otherwise known as arteriosclerosis), anterior uveitis and myointimal hyperplasia following angioplasty; thyroiditis, atherosclerotic heart disease, reperfusion injury, cardiac conduction disturbances, myocardial infarction, habitual abortion, retinitis pigmentosa, immune and inflammatory components of degenerative fundus disease, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, Guillaitn-Barre syndrome, myasthenia gravis, graft rejection in cases of transplantation of natural or artificial cells, tissue and organs such as cornea, bone marrow, organs, lenses, pacemakers, natural or artificial skin tissue.

In more detail: Organ-specific autoimmune diseases include multiple sclerosis and inflammatory bowel diseases (Crohn's disease, ulcerative colitis) for example.

Systemic autoimmune diseases include: rheumatoid arthritis.

Vascular disorders include vascular disorders in which there is inflammation of the intima of the blood vessels.

Suitably, the vascular disorders according to the present invention may include any vascular disease or disorder which comprises an autoimmune element, for example one which is caused by an autoimmune response.

Suitably, vascular disorders according to the present invention may include one or more of Raynaud's disease and phenomenon, anterior uveitis, obliterative vascular disorder, atheroma formation (otherwise known as arteriosclerosis), arteritis, myointimal hyperplasia (natural or following angioplasty), inflammatory and autoimmune thickening of the intima and/or muscular layer of blood vessels, inflammatory blood vessel lesions, atherosclerotic heart disease, reperfusion injury, cardiac conduction disturbances, myocardial infarction.

Suitably, the graft rejection according to the present invention may be chronic graft rejection, particularly in the absence of an immunosuppressant. Thus, the composition according to the present invention may be used as a replacement for the conventional immunosuppressant administered prior to, during and/or after transplantation. The compositions according to the present invention may be used when transplanting natural or artificial cells, tissues and organs, such as one or more of the following: corneas, bone marrow, organs (e.g. kidney, liver), lenses, pacemakers, natural or artificial skin tissue, islet cells.

Preferably, the compositions of the present invention may be used to treat the following autoimmune diseases: a vascular disorder, arthritis, graft rejection and the immunological aspects underlying myointimal hyperplasis and atheroma formation.

Stress

Stress is often presented as a symptom of modern living, the high pressure executive lifestyle, the consequences of which are widely perceived as leading to major pathological conditions such as gastric ulcers, hypertension, heart disease and strokes. Other major stressful events in life such as divorce, bereavement and moving house are seen as high risk factors for heart disease.

These are not misconceptions, the farming industry is well aware of the economic losses resulting from subjecting livestock to major stresses such as overcrowding, confinement and transportation leading to an increased susceptibility to infection and the precipitation of underlying pathology. Research by doctors and scientists is producing an increasing volume of published work showing definable stresses such as confinement can result in significant changes in endocrine (hormone) activity which subsequently can affect the body's immune functions. This can be noticeably demonstrated in major trauma stress (including surgical stress) in which the cell mediated immune response is dramatically paralysed Faist (1996).

Elenkov I J (1999) report recent evidence indicating that glucocorticoids and catecholamines, the end products of the stress system, and histamine, a product of activated mast cells, might selectively suppress cellular immunity, and favour humoral immune responses. This is mediated by a differential effect of stress hormones and histamine, on Th1/Th2 patterns and type 1/type 2-cytokine production. Thus, systemically, stress might induce a Th2 shift, while, locally, under certain conditions, it might induce pro-inflammatory activities through neural activation of the peripheral corticotrophin-releasing factor-mast cell-histamine axis.

Paik (2000) and Kay (2001) in independent studies of academic stress, examined the immunological profiles of students during non exam and exam periods. They report a significant reduction in IL-2 and interferon gamma production and an increase in IL-6.

This indicates that the body's immune system responds to stressful episodes by a down regulation of Th-I cytokines and a selective up-regulation of the Th2 cytokines.

Iwakabe (1998), using a mouse model of restraint stress reports the skewing of the immune response towards Th2 dominant immunity.

This stress hormone induced switch towards Th2 immune imbalance is also reported in non major, chronic stress situations such as psychosocial stress amongst workers overwintering at the Australian National Antarctic Research Expedition stations, (Mehta (2000)). They also report an associated increase in latent virus reactivations.

Similar stress hormone and immunological changes are reported from chronic stress in care givers of dementia patients (Bauer (2000)) and in astronauts during the Euromir 95 mission (Norbiato (1998)). Of particular concern was the astronauts increased susceptibility to infection.

The body is designed to recover from stress and in acute stress clearly does as the risk of infection recedes with the patient's recovery from the major trauma.

Chronic stress however appears to maintain the Th2 dominated immune imbalance. This is a very serious consequence as all of the quoted authors allude to stress through the above mechanisms, possibly influencing the onset and/or course of infectious, inflammatory, allergic and neoplastic diseases.

This consequence is further supported by Lawrence (2000).

An immunoregulator, preferably, an orally administered immunoregulator, according to the present invention, which stimulates the Th1 response and down regulates Th2 may restore the healthy balance of the immune system and thus reduce the increased risk of serious illness associated with chronic stress.

Preferably, the composition according to the present invention is used to treat and/or prevent stress, in particular major trauma stress, psychosocial stress and chronic stress.

Preferably, the composition according to the present invention is used to treat and/or prevent stress in animals, suitably in humans and/or livestock.

Immune System Imbalance

An immune system imbalance—such as an upregulation, downregulation or inappropriately regulated cellular immune response—may occur at any time in the life of a subject. Suitably, the compositions may be used to modulate an immune system imbalance. That is to say, the compositions according to the present invention may be used to treat and/or prevent an immune system imbalance.

(a) In Children

Suitably, the immune modulator composition or a pharmaceutical composition may be used to modulate an immune system imbalance, in children, including babies, infants and juveniles. An immune system imbalance—such as an upregulation, downregulation or inappropriately regulated cellular immune response—may occur in children following vaccination, for example following childhood vaccinations. Such an immune system imbalance may result in conditions such as the onset of allergies, i.e. allergic dermatitis and allergic asthma.

With the aim of protecting children from infections, repeated injections against Diphtheria, Tetanus, Pertussis, Polio, Measles, Mumps and the Rubella are given. All of these are judged necessary and pressure is exerted by Health authorities to ensure that children are presented for vaccination at the appropriate time. However, most vaccinations given in early life contain an alum adjuvant, which has important immunological consequences. Alum is a potent stimulus to the Th2 pattern of response and the consequential immune dysregulation causes the child to become vulnerable to the development of allergies and possibly cancer for example.

It is possible to re-educate the immune system to a proper recognition, regulation and response both to self and to the rest of the world.

Suitably, the immune modulator composition or a pharmaceutical composition may also be used for the treatment or prevention of an adverse reaction to childhood vaccines—such as whooping cough vaccinations and the current MMR vaccinations—and/or consequences thereof.

(b) Immune System Imbalance in the Elderly

An immune system imbalance—such as an upregulation, downregulation or inappropriately regulated cellular immune response, in particular downregulation, for example a deterioration of immune function—may occur in older people, generally in excess of 60 years. In elderly people, a downregulation in the cellular immune response is generally referred to as immuno senescence. Typically, the deterioration of immune function may lead to increased susceptibility to infectious diseases and neoplasia for example. The number of old people as a proportion of the population is dramatically increasing and geriatric medicine is becoming an important aspect of clinical practice. It is not surprising therefore that research has focused on the mechanisms of immunosenescence and the links between the health of the immune system and longevity. Goronzy (2001), examined the varying efficacy of influenza vaccination in the elderly. In this study, only 17% of subjects showed a rise in titre to all 3 haemagglutinins (successful vaccination) 1 month following vaccination and that 46% showed no demonstrable response at all. It was proposed that responsiveness to influenza vaccination is a useful biological marker of immunosenescence. A number of researchers have studied various aspects of the immune function in the elderly. For example, Lio (2000) studied cytokine responses, Solana (2000) studied NK and NKt cells, and Ginaldi (1999) suggested that a Th1 to Th2 cytokine production shift and an increased production of proinflammatory cytokines could explain many aspects of age-associated pathological events, such as atherosclerosis and osteoporosis. Accordingly, a non-pathological stimulation of the immune system which drives the cytokine response away from the proinflammatory Th2 towards Th1 is required. Preferably, such an immune modulator reduces the mortality from acute infection, counters the onset and reduces the morbidity of age related autoimmune disease and possibly reduces the rate of neoplastic disease, all of which are associated with immunosenescence.

Typically, an immune modulator composition or a pharmaceutical composition according to this aspect of the present invention may be an immune enhancer.

The potential role of probiotic commensal gut or dairy bacteria have been investigated in this area. For example, milk products supplemented with $5\times10^9$ or $5\times10^{10}$ *Bifidobacterium lactis* or *Lactobacillus rhamnosus* per dose taken daily for 3 weeks has been reported to increase the numbers of peripheral blood NK, CD4 and CD25 cells and generally boost systemic cellular immunity in the elderly (Gill, (2001)).

Currently a number of products containing high numbers of Lactobacilli and other intestinal commensal flora are being actively promoted as "lifestyle enhancers". A review by Sanders (2001), on the claimed probiotic effects of *Lactobacillus acidophilus*, available as a drug since 1950, suggests its effects require further validation and clarification of the mechanism of action. Whilst there is a beneficial effect from replacing the bowel flora after diarrhoeal disease and combating candidiasis following antibiotic therapy, immune stimulation appears unreliable and short lived. However, this work clearly identifies a role for a potent orally administered immune modulator, preferably killed so as to avoid the difficulties of maintaining live products.

Oral vaccination is a long established successful mechanism for inducing local protective immunity against oral/faecal pathogens—such as polio. However, orally administered vaccines have also been shown to evoke systemic protective immune responses both cell mediated and humoral. Sharpe (2002), used an orally administered adenovirus construct containing measles virus antigen to induce systemic antibody and splenic lymphocyte responses to the measles antigen. Manube (2002) has developed a model to show that orally administered attenuated *Mycobacterium microti* provides a higher level of protection to an aerosol challenge with tuberculosis than traditional subcutaneously administered BCG.

Kim (2001) showed that feeding with Japanese cedar pollen produced oral tolerance to specific allergy induced by subsequent injection of pollen in oil. This was associated with decreased specific immunoglobin levels and a significant reduction in interleukin-4 production i.e. the TH2 response was down-regulated.

Therefore, a systemic immune response may be both stimulated and modulated by administration—such as oral administration—of a suitable immune modulator.

Suitably, in one aspect of the present invention it is envisaged that a whole cell of the bacterium according to the present invention, may be included in food preparations and/or may be supplied as a type of "remedy", preferably orally.

Enhancing the Immune System

The compositions of the present invention may be used in the manufacture of a medicament for enhancing the immune system in an animal, preferably a mammal, more preferably livestock and/or racing animals, which may result in for example, enhancement (e.g. promotion) of growth and/or an increase in the efficiency of feed utilisation and/or a generally increased well-being (i.e. the overall health of the subject is improved) in the subject. The overall health of a subject can be determined by one or more of the following parameters for example: weight data (with weight gain being a positive determinant), alertness (with full alert being a positive determinant), movement (with energetic movement as opposed to lethargic movement being a positive determinant) and sickness (with reduced amount of sickness being a positive determinant). Typically, the immune modulator composition or pharmaceutical composition according to this aspect of the present invention may be an immune enhancer.

Advantageously, the immune modulator composition or pharmaceutical composition of the present invention may be used to replace antibiotics that are currently used to promote the growth of livestock.

The term "livestock", as used herein refers to any farmed animal. Preferably, livestock is one or more of poultry (including chickens), pigs (including piglets), sheep (including lambs), cows or bulls (including calves). More preferably, livestock means pigs—including piglets.

The present invention also contemplates the genera of the present invention being administered in combination with known probiotic bacteria, for modification of the cellular immune response.

Commercially at present antibiotics are commonly used as dietary enhancing feed additives (or growth promoters) and are incorporated into animal feed. However, the EU, is expected to introduce a complete ban on the non-clinical use of antibiotics in animal husbandry. Therefore, the market requires effective alternatives.

An advantage of the present invention is that it may be used (optionally together with good animal husbandry practices) as a replacement to dietary enhancing feed additive (or growth promoters).

The immune modulator compositions or pharmaceutical compositions of the present invention may be administered as a food additive when used to enhance the immune system.

Cancer

Suitably, the compositions according to the present invention are used to modulate a cellular immune response to treat and/or prevent cancer. In particular it is envisaged that the compositions according to the present invention may be used to protect a subject against developing and/or the progression of a cancer. In particular, the subject with a modulated cellular immune response may be less susceptible to the development of cancer.

In particular, during cancer growth an unregulated increase in Th2 is observed.

Cancer is a disease that affects many people, with 65 percent of cases occurring in those over 65. As the average life expectancy in the UK has almost doubled since the mid-nineteenth century, the population at risk of cancer has grown. Death rates from other causes of death, such as heart disease, have fallen in recent years while deaths from cancer have remained relatively stable. The result is that 1 in 3 people will be diagnosed with cancer during their lifetime and 1 in 4 people will die from cancer.

Examples of cancer include bladder, brain tumor, breast cancer, cervical cancer, colon and rectal cancer, adenocarcinoma, endometrial cancer, esophageal cancer, kidney cancer, leukaemia, liver cancer, lung cancer, melanoma, myeloma, non-hodgkin's lymphoma, ovarian cancer, pancreatic cancer, prostate cancer, sarcoma, soft tissue and stomach cancer.

In addition, persistent smoking of tobacco, and to a lesser, extent passive smoking, has been associated with carcinomas of the parts directly in contact with smoke, oropharynx, trachea, lungs, oesophagus and stomach. As well as these, distant tumours such as those of the kidney, bladder, pancreas, liver and myeloid leukaemia may be increase by smoking of tobacco. In the present invention, it is envisaged that compositions according to the present invention could be administered to smokers of tobacco in an attempt to reduce the smokers' risk of developing carcinomas associated with tobacco smoking.

Suitably, the cancer may be an adenocarcinoma or a melanoma.

Suitably, the cancer may be virally related cancers such as cervical cancer for example. Without wishing to be bound by theory, in some instances it has been found that an infection caused by papilloma viruses, such as dysplasia of the uterine cervix, precedes carcinoma of the cervix. Thus, cervical cancer is herein considered a "virally related cancer". However, the term "virally related cancer" as used herein means any cancer which may be caused by or related with a viral infection.

Post-Operative Recovery, Stress and Infection

Following any major operation a number of situations potentially arise:—

Stresses associated with a surgical operation include one or more of the following: apprehension before the operation, stress to the tissues due to the operative procedures, the pain usually accompanying recovery, worry about the significance of operative findings.

These kinds of stress are associated with the deviation of T-cell function towards Th2.

Immunosuppressive effects of premedication and anaesthetics, which may persist for days or weeks after the operation itself.

For the avoidance of doubt, the term "post-operative stress" as used herein includes the stress associated with anaesthesia.

In addition, exposure of cut flesh to direct infection at the time of operation and of the wound to infection in the recovery room and wards prior to leaving hospital is also a problem.

A combination of these factors exposes the patient to a series of potential bacterial infections, which:—

Since the patient is hospitalised, include such notorious hospital-associated infections as those with methicillin-resistant-*Staphylococcus aureus* (MRSA). Operations on the bowel expose the patient to gram-negative infections due to exposure of cut tissues to bowel contents. Operations on the lower limbs are also subject to infections with normal members of the gut flora.

Minor infections of the wound delay healing and increase the chances of contracting more serious infections.

To counteract these influences, immune regulation towards Th1 and a down-regulation of Th2 a result of the application of the invention, should do one or more of the following: increase non-specific resistance to post-operative bacterial infections; aid in wound healing and/or reduce stress.

T Helper Cells

The term 'Th1' as used herein refers to a type 1 T-helper cell (Th1). The term may also be used herein to refer to the response mediated by or through such a cell type. Such a response may include one or more of the secretion of Interleukin-2 (IL-2), the secretion of Interferon-gamma (IFN-γ), activation of macrophages, activation of cytotoxic T-cells, or any other Th1-associated event. Thus, the term 'Th1' may include Th1 cell(s) as well as the immune response(s) which such cell(s) produce.

The term 'Th2' as used herein refers to a type 2 T-helper cell (Th2). The term may also be used herein to refer to the response mediated by or through such a cell type. Such a response may include one or more of the secretion of Interleukin-4 (IL-4), the secretion of the splice variant interleukin IL-4δ2, the secretion of Interleukin-5 (IL-5), increase in levels of cell determinant 30 (CD30) on lymphocytes, increase in levels of Immunoglobulin-E (IgE) in the blood or eosinophils in the blood, or any other Th2-associated event. Thus, the term 'Th2' may include Th2 cell(s) as well as the immune response(s) which such cell(s) produce.

It is known that various conditions may result in or from an unregulated or inappropriately regulated cellular immune response, in particular in the activation and/or proliferation of Th1 and/or Th2, which if left unregulated or inappropriately regulated has been found to result in one or more detrimental effects on the subject.

In particular, such an unregulated or inappropriately regulated cellular immune response has been found to occur following vaccination, e.g. following childhood vaccinations, and is thought to result in conditions such as the onset of allergies, i.e. allergic dermatitis and allergic asthma. By way of example, Lewis D *Curr Opin Immunol* 2002; 14: 644 report that Th2 immune responses mediated by the secretion of IL-4, IL-5 and IL-13 are key in the pathogenesis of atopic disorders, including allergen-induced asthma, rhinoconjunctivitis and anaphylaxis. Although such responses are downregulated to some degree by conventional specific immunotherapy, this approach is only partially effective and has a substantial risk of adverse effects. Many strategies for immunotherapeutic prophylaxis and for treatment of atopic diseases have been devised on the basis of mouse allergy models, including the downregulation of Th2 responses by the induction of regulatory T cell activity, Th2 to Th1 immune deviation, Th1 crossregulation of Th2 immune responses, anergy and immunosuppressive cytokines. Choi & Koh *Ann Allergy Asthma Immunol* 2002; 88: 584-91 examined whether BCG vaccination of adult patients with asthma, a Th2-associated allergic disease, is clinically effective. It was shown that BCG vaccination improved lung function and reduced medication use in adults with moderate-to-severe asthma. This amelioration was accompanied by a suppressed Th2-type immune response, suggesting that BCG vaccination might be an effective therapeutic modality against asthma. von Hertzen *J Allergy Clin Immunol* 2002; 109: 923-8 outlined the possibility that prolonged maternal stress associated with sustained excessive cortisol secretion could affect the developing immune system—especially Th1/Th2 cell differentiation which may further increase the susceptibility to asthma and atopy in genetically predisposed individuals.

In addition, an unregulated or inappropriately regulated cellular immune response has been observed during disease progression. In particular during cancer growth an unregulated increase in Th2 is observed. By way of example, Maraveyas et al. *Ann Oncol* 1999; 10: 817-24 have studied the efficacy of SRL 172 vaccine in patients with cancer i.e. advanced stage IV (AJCC) malignant melanoma. Induction of intracellular cytokines (IL-2 and INF-gamma) in peripheral blood lymphocytes (PBLCs) from these patients was assayed and correlated to clinical outcome. It was demonstrated that SRL 172 was effective in inducing intracellular IL-2 responses in a significant number of patients with stage IV (AJCC) melanoma. Stanford et al. *International Journal of Pharmaceutical Medicine* 1999; 13: 191-195 report that there is increasing evidence that effective anti-tumour immune responses are likely to be mediated by type 1 cytokines. Recent investigations indicate that heat-killed *Mycobacterium vaccae*, is a reliable Th1 adjuvant and preliminary clinical trials indicate beneficial effects in melanoma, and cancer of the prostate and lung. More extensive controlled studies are currently being conducted to confirm these findings.

An unregulated or inappropriately regulated cellular immune response has also been observed during infection and particularly chronic infection, for example during progressive tuberculosis, lepromatous leprosy, visceral leishmaniasis and HIV infection and during allergies. By way of example, Clerici & Shearer G M *Immunol Today* 1993; 14: 107-11 propose that a Th1 to Th2 switch is a critical step in the etiology of HIV infection. Clerici & Shearer *Immunol Lett* 1996; 51: 69-73 show that HIV-specific cell mediated immunity may be the main correlator of protection against HIV infection and against the progression of HIV infection to AIDS. Abbot N C et al. *European Journal of Vascular and Endovascular Surgery* 2002 24:202-8 evaluated immunotherapy as a means of improving peripheral blood flow in chronic leprosy patients by administration of heat-killed *Mycobacterium vaccae*. It was shown that immunotherapy, given 18 months earlier, significantly improved blood flow and temperature sensation, in fully-treated, chronic, leprosy patients.

Accordingly, an aim of the present invention is to promote and establish the regulation of a cellular immune response, including the regulation or modulation of Th1 and/or Th2, in such a way so as to overcome the negative effects of the unregulated or inappropriately regulated cellular immune response.

Suitably, the use of an immune modulator composition and/or pharmaceutical composition according to the present invention modulates the Th1 or Th2 response, i.e. a Th1 or Th2 response that results in, for example, tissue damage.

An unregulated or inappropriately regulated immune response may play a role in the establishment of disease due to the fact that some diseases cause shifted Th1 and/or Th2 responses. Accompanying these atypical Th1 and Th2 reactions are a series of abnormal inflammatory responses, which may take part in the mechanisms underlying tissue pathology.

By way of example only, the immune modulator composition and/or pharmaceutical composition according to the present invention may counteract the disadvantages of reduced contact with environmental influences (for example, antigens) commensurate with modern life, may counteract the influence of treatment of an infection (e.g. a parasitic infection, such as, for example, malaria, trypanosomiasis, leishmaniasis, and toxoplasmosis) and/or the immunological abnormalities accompanying an infection, stress, such as, for example, major trauma stress, psychosocial stress and chronic stress, an allergy (e.g. asthma including asthma, allergic asthma, hayfever, allergic dermatitis (eczema), anaphylactic shock, allergies to plant contact or ingestion, stings—such as nettle and insect stings, and allergies to insect bites—such as midges for instance *Culicoides* (which causes Sweet Itch in horses), heaves, COPD and cancer (for example melanoma or adenocarcinoma); an immune system imbalance (e.g. an immune system imbalance in children e.g. the undesirable effect of childhood vaccines and the elderly); and post-operative stress and post-operative infection.

Vaccines

The preparation of vaccines which contain one or more substances as an active ingredient(s), is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the active ingredient(s) encapsulated in liposomes. The active ingredients are often mixed with excipients which are pharmaceutically acceptable and compatible with the active ingredient. Suitable excipients are, for example, water, saline, dextrose, glycerol, ethanol, or the like and combinations thereof. Alternatively, the vaccine may be prepared, for example, to be orally ingested and/or capable of inhalation.

In addition, if desired, the vaccine may contain minor amounts of auxiliary substances such as wetting or emulsifying agents and pH buffering agents.

Administration

Typically, a physician will determine the actual dosage of a vaccine, immune modulator composition and pharmaceutical composition which will be most suitable for an individual subject and it will vary with the age, weight and response of the particular patient. The dosages below are exemplary of the average case. There can, of course, be individual instances where higher or lower dosage ranges are merited.

Preferably, the actual dosage that is used results in minimal toxicity to the subject.

The compositions of the present invention may be administered by direct injection. The composition may be formulated for parenteral, mucosal, intramuscular, intravenous, subcutaneous, intraocular, intradermal or transdermal administration.

Suitably, the composition according to the present invention may be administered at a dose of $10^3$-$10^{11}$ organisms, preferably $10^4$-$10^{10}$ organisms, more preferably $10^6$-10-5×$10^9$ organisms, and even more preferably $10^6$-$10^9$ organisms. Typically, the composition according to the present invention may be administered at a dose of $10^8$-$10^9$ bacteria for human and animal use.

If the compositions of the present invention are to be administrated as immune enhancers, then $10^3$-$10^{11}$ organisms per dose, preferably $10^4$-$10^{10}$ organisms per dose, more preferably $10^6$-10-5×$10^9$ organisms per dose, and even more preferably $10^6$-$10^9$ organisms per dose, and even more preferably, $10^8$-$10^9$ bacteria per dose for human and animal use may be administered at regular intervals.

As will be readily appreciated by a skilled person the dosage administered will be dependent upon the organism to which the dose is being administered.

The term "administered" includes delivery by delivery mechanisms including injection, lipid mediated transfection, liposomes, immunoliposomes, lipofectin, cationic facial amphiphiles (CFAs) and combinations thereof, or even viral delivery. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular, intradermal or subcutaneous route.

The term "co-administered" means that the site and time of administration of each of the adjuvants(s), antigen(s) and/or antigenic determinant(s) of the present invention are such that the necessary modulation of the immune system is achieved. Thus, whilst the antigen(s) and adjuvant(s) may be administered at the same moment in time and at the same site, there may be advantages in administering the antigen(s) and/or antigenic determinant(s) at a different time and to a different site from the adjuvant(s). The antigen(s) and/or antigenic determinant(s) and adjuvant(s) may even be delivered in the same delivery vehicle—and the antigen(s) and/or antigenic determinant(s) and adjuvant(s) may be coupled and/or uncoupled and/or genetically coupled and/or uncoupled. By way of example only, the immune modulator composition according to the present invention may be administered before, at the same time or post administration of one or more antigens or further antigens.

The antigen, antigenic determinant, peptide or homologue or mimetic thereof may be administered separately or co-administered to the host subject as a single dose or in multiple doses.

The immune modulator composition and/or pharmaceutical composition of the invention may be administered by a number of different routes such as injection (which includes parenteral, subcutaneous, intradermal and intramuscular injection) intranasal, mucosal, oral, intra-vaginal, urethral or ocular administration.

Preferably, in the present invention, administration is by injection. More preferably the injection is intradermal.

Preferably, in the present invention, administration is by an orally acceptable composition.

For vaccination the composition can be provided in 0.1 to 0.2 ml of aqueous solution, preferably buffered physiological saline, and administered parenterally, for example by intradermal inoculation. The vaccine according to the invention is preferably injected intradermally. Slight swelling and redness, sometimes also itching may be found at the injection site. The mode of administration, the dose and the number of administrations can be optimised by those skilled in the art in a known manner.

Antigens

As used herein, an "antigen" means an entity which, when introduced into an immunocompetent host, modifies the production of a specific antibody or antibodies that can combine with the entity, and/or modifies the relevant Th response, such as Th2 and/or Th1. The antigen may be a pure substance, a mixture of substances or soluble or particulate material (including cells or cell fragments or cell sonicate). In this sense, the term includes any suitable antigenic determinant, cross reacting antigen, alloantigen, xenoantigen, tolerogen, allergen, hapten, and immunogen, or parts thereof, as well as any combination thereof, and these terms are used interchangeably throughout the text.

The term "antigenic determinant or epitope" as used herein refers to a site on an antigen which is recognised by an antibody or T-cell receptor, or is responsible for evoking the T-helper cell response. Preferably it is a short peptide derived from or as part of a protein antigen. However the term is also intended to include glycopeptides and carbohydrate epitopes. The term also includes modified sequences of amino acids or carbohydrates which stimulate responses which recognise the whole organism.

It is advantageous if the antigenic determinant is an antigenic determinant of the infectious agent which causes the infectious disease.

A "preventative" or "prophylactic" vaccine is a vaccine which is administered to naive individuals to prevent development of a condition, such as by stimulating protective immunity.

A "therapeutic" vaccine is a vaccine which is administered to individuals with an existing condition to reduce or minimise the condition or to abrogate the immunopathological consequences of the condition.

Adjuvants

The term 'adjuvant' as used herein means an entity capable of augmenting or participating in the influencing of an immune response. An adjuvant is any substance or mixture of substances that assists, increases, downregulates, modifies or diversifies the immune response to an antigen.

The immune modulator composition and/or pharmaceutical composition according to the present invention may comprise one or more adjuvants which enhance the effectiveness of the immune modulator composition and/or pharmaceutical compositions. Examples of additional adjuvants which, may be effective include but are not limited to: whole cells of a bacterium from one or more of the following genera *Tsukamurella, Rhodococcus, Gordonia, Nocardia, Dietzia, Mycobacterium*, aluminium hydroxide, aluminium phosphate, aluminium potassium sulphate (alum), beryllium sulphate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis, Mycobacterium vaccae, Mycobacterium obuense*, polyribonucleotides, sodium alginate, lanolin, lysolecithin, vitamin A, interleukins such as interleukin 2 and interleukin-12, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Only aluminium hydroxide is approved for human use. Some of the other adjuvants, such as *M. vaccae* for example, have been approved for clinical trials.

Suitably, the adjuvant may be a whole cell of a bacterium from a rough strain of *Mycobacterium obuense.*

In the art, it is known that DNA vaccines, which are essentially DNA sequences attached to gold particles and which are fired into the skin by a helium gun, are efficient vaccine delivery systems. Unlike conventional vaccines, these DNA vaccines do not require a traditional adjuvant component. In accordance with a further aspect of the present invention, the immune modulator composition as defined herein may suitably be used in conjunction with such DNA vaccines to augment or participate in the influencing of the immune response.

Pharmaceutical Compositions

The present invention also provides a pharmaceutical composition comprising a therapeutically effective amount of a whole cell of a bacterium from a rough strain of *Mycobacterium obuense* and optionally a pharmaceutically acceptable carrier, diluent or excipients (including combinations thereof).

The pharmaceutical composition may comprise two components—a first component comprising an antigen and a second component comprising an adjuvant thereof. The first and second component may be delivered sequentially, simultaneously or together, and even by different administration routes.

Suitably, the antigen may even be engendered within the host tissues as part of a disease process. Thus, antigen may originate from a bacterial, host or parasitic invasion, or may be a substance release from the tissues such as a stress protein or a tumour antigen.

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a mini-pump or by a mucosal route, for example, as a nasal spray or aerosol for inhalation or ingestable solution, or parenterally in which the composition is formulated by an injectable form, for delivery, by, for example, an intravenous, intramuscular, intradermal or subcutaneous route. Alternatively, the formulation may be designed to be delivered by both routes.

Preferably in the present invention the formulation is of injectable form. More preferably the formulation is intradermally injected.

Preferably in the present invention the formulation is an orally acceptable composition.

Where the agent is to be delivered mucosally through the gastrointestinal mucosa, it should be able to remain stable during transit through the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly, intradermally or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Pharmaceutical Combinations

The agent of the present invention may be administered with one or more other pharmaceutically active substances. By way of example, the present invention covers the simultaneous, or sequential treatments with an immune modulator composition and/or pharmaceutical composition according to the present invention, and one or more steroids, analgesics, antivirals, interleukins such as IL-2, or other pharmaceutically active substance(s).

It will be understood that these regimes include the administration of the substances sequentially, simultaneously or together.

Immune Enhancer

The term "immune enhancer" as used herein means one or more bacteria either isolated or in culture which when administered to a subject benefit the health of that subject. Preferably, this benefit is achieved by the modification of the cellular immune response of the subject.

In accordance with the present invention, immune enhancers may be used, for example, for the treatment or prevention of an immune system imbalance in a subject, preferably a child or an elderly subject, or for enhancing the immune system of a subject, for example of a mammal, particularly of livestock or of humans.

The immune enhancers may be administered by consumption in specially designed food or in animal feeds, for example pig animal feeds supplemented with the bacteria of the present invention.

The immune enhancers may also be administered by other routes—such as direct injection.

Preferably, the bacteria are killed so as to avoid the difficulties of maintaining live products.

Identifying a Bacterium that Modulates a Cellular Immune Response

In another aspect, the present invention relates to a method for identifying one or more whole cells of bacteria from a rough strain of *Mycobacterium* that modulate (e.g. modify) a cellular immune response comprising the steps of: (a) contacting a first test animal with an immunostimulant; (b) contacting a second test animal with an immunostimulant mixed with a bacterium; (c) measuring the cellular immune response in each of the test animals; and (d) comparing the cellular immune response in each of the test animals, wherein, a lower cellular immune response from the immunostimulant mixed with a bacterium in comparison to the immunostimulant alone is indicative of a modification of the cellular immune response by the bacterium.

In another aspect, the present invention relates to a method of determining the Th1/Th2 response of a rough strain of bacteria selected from the genus *Mycobacterium* which method comprises utilisation of the tuberculin skin test. In mice, the tuberculin skin test is preferably carried out on the foot pad. In a predominant Th1 reaction the positive foot pad immune response is maximal at 24 hours and diminishes at 48 hours. However, as the Th2 reactivity increases then the 48 hour positive foot pad immune response increases and can even exceed the foot pad immune response at 24 hour.

The effect of BCG vaccination is well documented using this tuberculin skin test. Thus, the test assay can be used to assess whether or not the introduction of an immune modulator composition according to the present invention modulates the BCG cellular immune response.

As used herein, the term "test animal" refers to any animal that elicits a cellular immune response to the immunostimulant. Preferably, the test animal(s) is a mammal. More preferably, the test animal(s) is a rat, hamster, rabbit, guinea pig or mouse. More preferably, the test animal(s) is a mouse.

Preferably, the bacterium modifies the T helper cell response. Suitably, the bacterium may modify the T helper cell response by decreasing the Th1 and Th2 response. Suitably, the bacterium may modify the T helper cell response by increasing the Th1 response and decreasing the Th2 response. Suitably, the bacterium may modify the T helper cell response by increasing the Th1 response without affecting the Th2 response.

Preferably, the immunostimulant will have a known Th1 and Th2 response. For example, with the immunostimulant BCG the reaction is usually largest at 24 h when it is an indicator of the Th1 response; the reaction at 48 h is usually less and includes a Th2 contribution. It is known that BCG predominantly stimulates a Th1 response.

By use of such immunostimulants it may be possible to determine the Th1/Th2 response of a test bacterium and, thus, it may be possible to identify one or more bacteria which have a desired Th1/Th2 response to treat and/or prevent a particular disease and/or disorder.

Preferably, the cellular immune response is measured using the tuberculin skin test. Vaccination with an immunostimulant—such as BCG—induces a response to skin-testing with tuberculin (a soluble preparation of *Tubercle bacilli*), when tested later. The local reaction is measured at various intervals, for example, 24 hours, 48 hours and 72 hours after injection of tuberculin. Briefly, an immunostimulant (e.g. BCG) is used that induces a positive immune response to tuberculin. In the test animal, the tuberculin skin test is preferably carried out on the foot pad. In a predominant Th1 reaction the positive foot pad immune response is usually maximal at 24 hours and diminishes at 48 hours. However, as the Th2 reactivity increases then the 48 hour positive foot pad immune response increases and can even exceed the foot pad immune response at 24 hour. Thus, the assay can be used to assess whether or not the introduction of an immune modulator composition according to the present invention modulates the cellular immune response.

Preferably, the immunostimulant is BCG.

The invention will now be further described by way of Examples, which are meant to serve to assist one of ordinary skill in the art in carrying out the invention and are not intended in any way to limit the scope of the invention.

EXAMPLES

Methods

Tuberculin Skin Test

The tuberculin skin test is an appropriate model assay to assess the effect of an immune modulator composition, i.e. bacterial compositions/suspensions comprising whole killed bacterial cells according to the present invention, on a cellular immune response.

BCG vaccination induces a positive immune response to tuberculin. In mice, the tuberculin skin test is preferably carried out on the foot pad. In a predominant Th1 reaction the positive foot pad immune response is maximal at 24 hours and diminishes at 48 hours. However, as the Th2 reactivity increases then the 48 hour positive foot pad immune response increases and can even exceed the foot pad immune response at 24 hour.

The effect of BCG vaccination is well documented using this tuberculin skin test. Thus, the test assay can be used to assess whether or not the introduction of an immune modulator composition according to the present invention modulates the BCG cellular immune response.

Preparation of a Bacterial Suspension

The bacteria of a rough strain from the genus *Mycobacteria* may be grown in an antigen-free medium, such as Sauton's medium, in a fermenter for 2-28 days. Alternatively, the bacterial species of interest may be grown on a solid slope. Alternative methods would be readily available to those skilled in the art.

The resulting bacterial mass may be harvested and either used directly or after washing to make a suspension in buffer. The bacterial cell suspension is prepared to contain between 100,000 and 10,000,000,000 bacilli per dose. The bacterial cells are resuspended in water or in a saline. Preferably, the saline is buffered at pH 8.0 with borate. Preferably the bacilli are inactivated (killed), suitably by heating in an autoclave for 15 minutes at 121° C. The resulting bacterial suspension comprises whole cells.

Example 1

Induction of a Stable Rough Variant of *Mycobacterium obuense* Type Strain (ATCC 27023)

*Mycobacterium obuense* type strain ATCC 27023 is only represented by this strain in the international collections. The strain is smooth in cultural character and is not known to throw rough variants.

Experiment 1.
Culture on to Middlebrook 7H11 Agar.

Six consecutive subcultures of *Mycobacterium obuense* type strain ATCC 27023 onto Middlebrook 7H11 agar produced smooth colonies only.

Experiment 2.
Culture on to Middlebrook 7H11 Agar with Different Concentrations of Added 4,4'-Diaminodiphenyl Sulfone Experiment 2, Part a
*Mycobacterium obuense* type strain ATCC 27023 was grown Middlebrook 7H11 medium comprising different concentrations of Dapsone™. Results are recorded in Table 1.

TABLE 1

Growth on different Dapsone ™ concentrations/ml of Middlebrook 7H11 medium

| μg Dapsone ™/ml Middlebrook 7H11 medium | Observed growth |
|---|---|
| 50 | no growth |
| 40 | no growth |
| 20 | no growth |
| 10 | no growth |
| 5 | 3 smooth colonies |
| 0 | confluent smooth growth |

Experiment 2, Part b
*Mycobacterium obuense* type strain ATCC 27023 was grown Middlebrook 7H11 medium comprising different concentrations of Dapsone™. Results are recorded in Table 2.

TABLE 2

Growth on different Dapsone ™ concentrations/ml of Middlebrook 7H11 medium.

| μg Dapsone ™/ml Middlebrook 7H11 medium | Observed growth |
|---|---|
| 5 | small smooth colonies |
| 4 | small smooth colonies |
| 3 | confluent smooth colonies |
| 0 | confluent smooth colonies |

Experiment 2, Part c
*Mycobacterium obuense* type strain ATCC 27023 was grown Middlebrook 7H11 medium comprising different concentrations of Dapsone™. Results are recorded in Table 3.

TABLE 3

Growth on different Dapsone ™ concentrations/ml of Middlebrook 7H11 medium.

| μg Dapsone ™/ml Middlebrook 7H11 medium | Observed growth |
|---|---|
| 12 | mostly rough colonies |
| 10 | mostly rough colonies |
| 7.5 | few rough colonies, mostly smooth colonies |
| 5 | few rough colonies, mostly smooth colonies |
| 0 | confluent smooth colonies |

Rough colonies were carefully picked off from the 12 μg Dapsone™/ml culture and subcultured repeatedly on Middlebrook 7H11 medium with no added Dapsone™

Only rough colonies have grown after 20 repeated subcultures (i.e. successional cultures).

The rough strain isolated using this experiment has been deposited with the NCTC under the Budapest Convention under accession number NCTC 13365.

Example 2

DTH Reactions to Tuberculin in BCG-Challenged Mice which Had been Treated with *M. obuense*

The experimental group was given, $10^7$ bacilli/0.1 ml of the immunomodulator, at birth and 21 days later (the time of weaning). Control mice received buffered borate under the same schedule.

Thirty days following the last immunisation mice were vaccinated into the scruff of the neck with BCG subcutaneously (Merieux) $10^5$ bacilli/0.1 ml Twenty eight days later animals were challenged with tuberculin (right hind footpad) or saline (left hind footpad) 0.02 ml.

Alternatively, the foot pad thickness can be measured before testing instead of injecting the left hind footpad, as well.

DTH reactions were measured at 24, 48 and 72 h post-challenge

| | Individual data | | |
|---|---|---|---|
| GROUP | 24 h | 48 h | 72 h |
| Borate | 0 | 0 | 0 |
| Borate | 14 | 3 | 7 |
| Borate | 12 | 22 | 25 |
| Borate | 15 | 12 | 13 |
| Borate | 4 | 1 | 6 |
| Borate | 0 | 0 | 0 |
| Borate | 0 | 0 | 0 |
| Borate | 10 | 4 | 3 |
| Borate | 13 | 12 | 14 |
| *M. obuense* NCTC 13365 | 1 | 1 | 1 |
| *M. obuense* NCTC 13365 | 1 | 2 | 2 |
| *M. obuense* NCTC 13365 | 2 | 6 | 4 |
| *M. obuense* NCTC 13365 | 0 | 4 | 2 |
| *M. obuense* NCTC 13365 | 5 | 6 | 14 |
| *M. obuense* NCTC 13365 | 6 | 6 | 9 |
| *M. obuense* NCTC 13365 | 0 | 0 | 0 |
| *M. obuense* NCTC 13365 | 1 | 4 | 4 |

-continued

| Individual data | | |
|---|---|---|
| Hours | Borate (n = 9) | *M. obuense* (n = 8) |
| 24 | 7.5 ± 2.16 | 2 ± 0.8 |
| 48 | 6 ± 2.57 | 3.6 ± 0.85 |
| 72 | 7.5 ± 2.8 | 4.5 ± 1.66 |

Values are means ± sem

There are no significant differences when non-responders and responders are pooled in this way.

However, when responders alone are analysed, significant differences are disclosed.

| Hours | 24 | 48 | 72 |
|---|---|---|---|
| Borate | 11.33 ± 3.98 | 10.60 ± 7.67 | 11.33 ± 7.92 |
| Mean +ve response size | n = 6 | n = 5 | n = 6 |
| *M. obuense* | 2.50 ± 2.43 | 4.67 ± 1.63 | 5.83 ± 4.75 |
| Mean +ve response size | n = 6 | n = 6 | n = 6 |

Differences in +ve response sizes to tuberculin between the borate-primed control and the results after priming with a rough strain of *M. obuense* are statistically significant at 24 hours ($p<0.005$) and although significance is lost at 48 and 72 hours, there is a downward trend.

A positive response to tuberculin means that effective cells have been drawn to the site of injection and that inflammatory cytokines have been released. Thus, in a negative response in which cells have been recruited to the site, but have not released cytokines, swelling, which is due chiefly to the response to released cytokines may not be appreciable, even though competent cells have been recruited to the site.

In an animal that has been immunised with reagents containing antigens shared with the test reagent, a lack of response does not mean that there is no response, just that the test has not detected it. Negative response may occur because there is an incapability of responding or there is a response but in a negative sense. The latter circumstance may be likely to happen in DTH reactions in BCG-challenged animals. Without wishing to be bound by theory, it is believed that sensitised cells may remain in lymph nodes instead of migrating to the dermis or that they may get there but produce downregulating cytokines, anergy-inducing cells. Sometimes, an alternative test such as the lymphocyte transformation test can demonstrate the presence of competent circulating cells responsive to the test antigen, and punch biopsies of apparently negative skin-test sites will show infiltrations of these cells, which nonetheless are not producing a perceptible swelling. The proportion of test-negative individuals, skin- or footpad-tested, varies with genetics and time scale in relation to priming and challenge. There is a large body of published evidence dealing with these phenomena in man.

Thus in analysis of data from such tests, one needs to look at proportion making a positive response and mean diameter of positive responses, as we have done. There was no difference in percent responding between the 2 groups, but there was a difference in the sizes of response that responders made.

CONCLUSIONS

*M. obuense* (rough strain NCTC 13365) has an immunoregulatory effect.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and immunology or related fields are intended to be within the scope of the following claims.

REFERENCES

Goronzy J J, Fulbright J W, Crowson C S, Poland G A, O'Fallon W M, Weyand C M. Value of immunological markers in predicting responsiveness to influenza vaccination in elderly individuals. J Virol 2001 December; 75(24): 12182-7

Lio D, Balistreri C R, Candore G, D'Anna C, Di Lorenzo G, Gervasi F, Listi F, Scola L, Caruso C. In vitro treatment with interleukin-2 normalizes type-1 cytokine production by lymphocytes from elderly. Immunopharmacol Immunotoxicol 2000 May; 22(2): 195-203

Solana R, Mariani E. NK and NK/T cells in human senescence. Vaccine 2000 Feb. 25; 18(16):1613-20

Ginaldi L, De Martinis M, D'Ostilio A, Marini L, Loreto M F, Quaglino D. The immune system in the elderly: III. Innate immunity. Immunol Res 1999; 20(2): 117-26

Gill H S, Rutherford K J, Cross M L. Dietary probiotic supplementation enhances natural killer cell activation in the elderly: an investigation of age-related immunological changes. J Clin Immunol 2001 July; 21(4): 264-71

Gill H S, Rutherford K J, Cross M L, Gopal P K. Enhancement of immunity in the elderly by dietary supplementation with the probiotic *Bifidobacterium* lactis HN019. Am. J. Clin. Nutr. 2001 December; 74(6):833-9.

de Roos N M, Katan M B. Effects of probiotic bacteria on diarrhoea, lipid metabolism, and carcinogenisis; a review of papers published between 1988 and 1998. Am. J. Clin. Nutr. 2000 February; 71(2):405-11.

Sanders M E, Klaenhammer T R. Invited review; the scientific basis of *Lactobacillus acidophilus* NCFM functionally as a probiotic. J Dairy Sci 2001 February; 84(2): 19-31

Sharpe S, Fooks A, Lee J, Clegg C, Cranage M. Single oral immunisation with replication deficient recombinant adenovirus elicits long-lived transgene-specific cellular and humoral Manabe Y C, Scott C P, Bishai W R. Naturally attenuated orally administered *Mycobacterium microti* as a tuberculosis vaccine is better than subcutaneous *Mycobacterium bovis* BCG.

Kim J H, Mini Y J, Ahn S H, Park J S, Woo W H. Induction of oral tolerance to Japanese cedar pollen. Arch Pharm Res 2001 December; 24(6):557-63

Elenkov I J, Chrousos G P Stress Hormones, Th1/Th2 patterns, Pro/Anti-inflammatory Cytokines and Susceptibility to Disease. Trends Endocrinol Metab 1999 November; 10(9):359-368

Faist E, Schinkel C, Zimmer S. Update on the mechanisms of immune suppression of injury and immune modulation. World J Surg 1996 May; 20(4):454-9

Paik I H, Toh K Y, Lee C, Kim J J, Lee S J. Psychological stress may induce increased humoral and decreased cellular immunity. Behav Med 2000 Fall; 26(3):139-41

Kang D H, Fox C Th1 and Th2 cytokine responses to academic stress. Res Nurs Health 2001 August; 24(4):245-57

Iwakabe k, Shimade m, Ohta A, Yahata T, Ohmi Y, habu S, Nishimura T. The restraint stress drives a shift in Th1/Th2 balance towards Th2-dominant immunity in mice. 1 mmol lett 1998 May; 62(1):39-43

Mehta S K, Pierson D-L, Cooley H, Dubow R, Lugg D. Epstein-Barr virus reactivation associated with diminished cell-mediated immunity in Antarctic expeditioners. J. Med. Virol. 2000. June; 61(2); 235-40

Bauer M E, Vedhara K, Perks P, Wilcock G K, Litman S L, Shanks N. Chronic stress in caregivers of dementia patients is associated with reduced lymphocyte sensitivity to glucocorticoids. J. Neuroimmonol. 2000 feb 1; 103(1):84-92

Norbiato G, Vago T, Battocchio L. Microbial and fungal contamination contributes to physical stress in space flight: studies in the Euromir-95 mission. J Gravit Physiol 1998 July; 5(1):P145-6

Elenkov I J, Chrousos G P. Stress, cytokine patterns and susceptibility to disease. Baillieres Best Pract Res Clin Endocrinol Metab 1999 December; 13(4):583-95

Lawrence D A, Kim D. Central/peripheral nervous system and immune responses. Toxicology 2000 Jan. 17; 124(3): 189-201

The invention claimed is:

1. A method eliciting an immune response in a subject having cancer, comprising administering a composition comprising a stable rough strain of *Mycobacterium obuense*.

2. A method according to claim 1, wherein the cancer is selected from the group consisting of bladder, brain tumor, breast cancer, cervical cancer, colon and rectal cancer, adenocarcinoma, endometrial cancer, esophageal cancer, kidney cancer, leukaemia, liver cancer, lung cancer, melanoma, myeloma, non-hodgkin's lymphoma, ovarian cancer, pancreatic cancer, prostate cancer, sarcoma, soft tissue and stomach cancer.

3. A method according to claim 1, wherein the cancer is an adenocarcinoma or a melanoma.

4. A method according to claim 1, wherein the cancer is a virally-related cancer.

5. A method according to claim 1, wherein the composition comprises a pharmaceutically acceptable carrier, diluent or excipient.

6. A method according to claim 1, wherein the rough strain downregulates a Th2 response.

7. A method according to claim 1, wherein the rough strain downregulates a Th2 response and upregulates a Th1 response.

8. A method according to claim 1, wherein the *Mycobacterium obuense* is a whole cell.

* * * * *